United States Patent
Eckert et al.

(10) Patent No.: US 9,826,618 B2
(45) Date of Patent: Nov. 21, 2017

(54) DEVICES FOR CONTROLLING NON-THERMAL PLASMA EMITTERS

(71) Applicant: ChiScan Holdings, LLC, Las Vegas, NV (US)

(72) Inventors: Bradley N. Eckert, Chandler, AZ (US); Huan Truong, Chandler, AZ (US); Bryon K. Eckert, Chandler, AZ (US)

(73) Assignee: ChiScan Holdings, LLC, Las Vegas, NV (US)

( * ) Notice: Subject to any disclaimer, the term of this patent is extended or adjusted under 35 U.S.C. 154(b) by 0 days.

(21) Appl. No.: 15/213,201

(22) Filed: Jul. 18, 2016

(65) Prior Publication Data
US 2017/0094769 A1  Mar. 30, 2017

Related U.S. Application Data

(63) Continuation-in-part of application No. 15/055,028, filed on Feb. 26, 2016, now Pat. No. 9,572,241.
(Continued)

(51) Int. Cl.
*H05B 37/02* (2006.01)
*H05H 1/24* (2006.01)
(Continued)

(52) U.S. Cl.
CPC ......... *H05H 1/2406* (2013.01); *A61B 18/042* (2013.01); *H05H 2001/2412* (2013.01); *H05H 2001/481* (2013.01); *H05H 2240/20* (2013.01)

(58) Field of Classification Search
CPC ..... A61B 18/042; A61N 1/40; H05H 2240/20
See application file for complete search history.

(56) References Cited

U.S. PATENT DOCUMENTS 5,329,496 A * 7/1994 Smith .................... B06B 1/064
                                                310/334
6,284,983 B1   9/2001 Lutschounig
(Continued)

FOREIGN PATENT DOCUMENTS

JP         2002151480        5/2002

OTHER PUBLICATIONS

Alekseev, Oleg et al., Nonthermal Dielectric Barrier Discharge (DBD) Plasma Suppresses Herpes Simplex Virus Type 1 (HSV-1) Replication in Corneal Epithelium, TVST, 2014, pp. 1-14, vol. 3, No. 2.
(Continued)

*Primary Examiner* — Don Le
(74) *Attorney, Agent, or Firm* — Quarles & Brady LLP

(57) ABSTRACT

An AC power supply drives and controls an array of non-thermal plasma emitters at desired frequencies at a controlled power level. The power supply comprises a step-up transformer, a balanced driver, and a controller. The transformer operates at the resonant frequency of the combined capacitance of the array and the cable connecting the array to the power supply. The power into the array is monitored by the controller and can be adjusted by the user. The balanced driver may be driven directly by the controller. The controller monitors the phase relationship between the transformer primary winding voltage and the gate drive voltage, and adjusts the drive frequency to resonance. Alternatively, the balanced driver is configured as an oscillator which drives the transformer at resonance by default. A signal from the transformer driver generates an interrupt to the controller for synchronizing current and voltage measurements for power control.

18 Claims, 16 Drawing Sheets

Related U.S. Application Data

(60) Provisional application No. 62/235,517, filed on Sep. 30, 2015.

(51) Int. Cl.
*A61B 18/04* (2006.01)
*H05H 1/48* (2006.01)

(56) References Cited

U.S. PATENT DOCUMENTS

| | | | |
|---|---|---|---|
| 7,280,874 | B2 | 10/2007 | Boehm |
| 7,305,935 | B1 | 12/2007 | Foster |
| 8,179,032 | B2 | 5/2012 | Eden et al. |
| 9,306,533 | B1* | 4/2016 | Mavretic ............... H03H 7/40 |
| 2003/0052096 | A1 | 3/2003 | Crowe et al. |
| 2006/0247737 | A1* | 11/2006 | Olson ................ A61N 1/3787 607/61 |
| 2010/0036369 | A1* | 2/2010 | Hancock ................ A61N 5/04 606/33 |
| 2010/0049261 | A1* | 2/2010 | Bare ..................... H04L 27/04 607/1 |
| 2010/0145253 | A1* | 6/2010 | Gutsol ................ A61B 18/042 604/20 |
| 2011/0140607 | A1* | 6/2011 | Moore ................ A61B 18/042 315/111.21 |
| 2012/0259270 | A1 | 10/2012 | Wandke |
| 2013/0038199 | A1 | 2/2013 | Roy |
| 2013/0345620 | A1* | 12/2013 | Zemel ................ A61B 18/042 604/24 |
| 2014/0217882 | A1 | 8/2014 | Yagi |
| 2014/0303549 | A1* | 10/2014 | Sheperak ................ A61N 5/10 604/24 |
| 2015/0146502 | A1* | 5/2015 | Kato ..................... B06B 1/0292 367/137 |
| 2015/0157870 | A1 | 6/2015 | Kalghatgi et al. |
| 2016/0128759 | A1* | 5/2016 | Long ..................... A61B 18/12 606/41 |

OTHER PUBLICATIONS

Algwari, Q.T. et al., Cold plasma jet developed that could kill superbugs, PLoS One, 2012, vol. 7, No. 8.
Arora, V. et al., Cold Atmospheric Plasma (CAP) in Dentistry, Dentisty, 2014, pp. 1-5, vol. 4, No. 1.
Barekzi, Nazir, Dose-dependent killing of leukemia cells by low-temperature plasma, Journal of Physics D Applied Physics, 2012, pp. 1-6, vol. 45.
Boonyawan, Dheerawan, Non-Thermal Plasma for Acne and Aesthetic Skin Improvement, Plasma Medicine, Jan. 2014, pp. 79-88, vol. 4. No. 1-4.
Boxhammer, V. et al., Investigation of the mutagenic potential of cord atmospheric plasma at bactericidal dosages, Mutation Research/Fundamental and Molecular Mechanisms of.
Byrne, Christopher et al., The ingestible telemetric body core temperature sensor: a review of validity and exercise applications, Sports Med, 2007, pp. 126-133, vol. 41.
Cahill, Orla et al., Cold Air Plasma to Decontaminate Inanimate Surfaces of the Hospital Environment, American Society for Microbiology, 2014, pp. 1-29.
Cahill, Orla et al., Cold Air Plasma to Decontaminate Inanimate Surfaces of the Hospital Environment, Applied and Environmental Microbiology, Mar. 2014, pp. 2004-2011, vol. 80, No. 6.
Cheng, Xiaoqian et al., The Effect of Tuning Cold Plasma Composition on Glioblastoma Cell Viability, PoLS One, 2014, pp. 1-9, vol. 9, No. 5.
Crozes, Gill et al., Synergies of UV Disinfection and Ozone in Water Treatment, International UV Association, 2003, pp. 1-5, Vienna, Austria.
Daeschlein, Georg et al., Plasma meets Dermatology: Clinical aspects in preventive and curative Medicine, German Federal Ministry of Education and Research (grant No. 13N9773 and 13N9779).

Dobrynin, Danil et al., Fast Blood Coagulation of Capillary Vessels by Cold Plasma: A Rat Ear Bleeding Model, Plasma Medicine, 2011, pp. 241-247, vol. 1, Philadelphia, Pennsylvania.
Dobrynin, Danil et al., Physical and biological mechanisms ot direct plasma interaction with living tissue, Institute of Physics, New Journal of Physics, 2009, pp. 1-26, vol. 11.
Dowling, Denis, Plasma medicine—new technology for anti-ageing and wound healing, Applied and Environmental Microbiology, 2013.
Erfurt-Berge, Cornelia et, Recent Developments in Topical Wound Therapy: Impact of Antimicrobiological Changes and Rebalancing the Wound Milieu, BioMed Research International, 2014, pp. 1-8.
Ferrell, James et al., Characterization, Properties and Applications ot Nonthermal Plasma: A Novel Pulsed-Based Option, Biotechnol Biomater, 2013, pp. 1-10, vol. 3, No. 2.
Fridman, Alexander et al., Plasma Medicine, book published in 2013, Chapters 1-4, 6-10, Wiley.
Fridman, Gregory et al., Floating Electrode Dielectric Barrier Discharge Plasma in Air Promoting Apoptotic Behavior in Melanoma Skin Cancer Cell Lines, Drexel University College of Engineering.
Fulton, Judith, Sterilization of Infected Wounds with Non-thermal Plasma, Akron General Medical Center, Presented at: Consortium for Wound Healing Research and Education.
Graves, David, Low temperature plasma biomedicine: A tutorial review, Physics of Plasmas, 2014, pp. 1-12, vol. 21.
Guceri, Selcuk et al., Plasma Assisted Decontamination of Biological and Chemical Agents, NATO Science for Peace and Security Series A: Chemistry and Biology.
Gupta, Aditya et al., Device-based Therapies for Onychomycosis Treatment, Skin Therapy Letter, 2012, vol. 17, No. 9.
Haertel, Beate et al., Non-Thermal Atmospheric-Pressure Plasma Possible Application in Wound Healing, Biomolecules and Therapeutics, The Korean Society of Applied Pharmacology, 2014, pp. 477-490.
Hameroff, Stuart, Ultimate Computing, Biomolecular Consciousness and NanoTechnology, Elsevier Science Publishers, Tucson, AZ.
Heinlin, Julia et al., Plasma medicine: possible applications in dermatology, The Authors Journal compilation Blackwell Verlag GmbH, 2010, pp. 1-9.
Hensel, Karol et al., Plasma for bio-decontamination, medicine and food security, NATO Advanced Research Workshop, 2011, Presented in Jasna, Slovakia.
Hermann, Hans et al., Chemical Warfare Agent Decontamination Studies in the Plasma Decon Chamber, IEEE Transactions on Plasma Science, 2002, pp. 1460-1471, vol. 30, No. 4.
Hirst, A.M. et al., Low-temperature plasma treatment induces DNA damage leading to necrotic cell death in primary prostate epithelial cells, British Journal of Cancer, 2015, pp. 1536-1545, vol. 112.
Hirst, A.M. et al., Low-temperature plasma treatment induces DNA damage leading to necrotic cell death in primary prostate epithelial cells, British Journal of Cancer, 2015, pp.
Hoffmann, Clotilde et al., Cold Atmospheric Plasma: methods ot production and application in dentistry and oncology, Medical Gas Research, 2013, pp. 1-15 vol. 3, No. 21.
Isbary, G., Cold atmospheric argon plasma significantly decreases bacterial load of chronic infected wounds in patients, Klinkum Schwabing.
Isbary, G. et al., Cold atmospheric plasma devices for medical issues, Expert Review of Medical Devices, 2013, pp. 376-377, vol. 10, No. 3.
Isbary, G. et al., Cold atmospheric plasma: A successful treatment of lesions in Hailey-Hailey disease, Archives of Dermatology, 2011, pp. 368-390, vol. 147, No. 4.
Isbary, G. et al., Non-thermal plasma—More than five years of clinical experience, Clinical Plasma Medicine, 2013, pp. 19-23, vol. 1.
Jeong-Hae, Choi et al., Low-temperature atmospheric plasma increases the expression of anti-aging genes of skin cells without causing cellular damages, Original Paper, Springer, 2012, pp. 1-8.

(56) References Cited

OTHER PUBLICATIONS

Jhang, Hogun, Effects of radio frequency waves on dissipative low frequency instabilities in mirror plasmas, 32nd EPS Conference on Plasma Phys. Tarragona, Jun. 27-Jul. 1, 2005 ECA vol. 29C, P-1.055.
Jiang, Weiman et al., Characterization of argon direct-current glow discharge with a longitudinal electric field applied at ambient air, Scientific Reports, 2014, pp. 1-6, vol. 4, No. 6323.
Joerres, Kyle, Characterization of Cold Atmospheric Plasma, Milwaukee School of Engineering, National Science Foundation Grant, Jun. 1-Aug. 8, 2014.
Joh, Hea Min, Effect of additive oxygen gas on cellular response of lung cancer cells induced by atmospheric pressure helium plasma jet, Scientific Reports, 2014, pp. 1-9, vol. 4, No. 6638.
Kalghatgi, S. et al., Transdermal drug delivery using cold plasmas, 22nd International Symposium on Plasma Chemistry Jul. 5-10, 2015; Antwerp, Belgium.
Karol Hensel and Zdenko Machala Editors, Book of Abstracts: NATO Science Advanced Research Workshop on Plasma for biodecontamination, medicine and food security, Mar. 15-18, 2011, Jasné, Slovakia.
Klampfl, Toblas, Cold Atmospheric Air Plasma Sterilization against Spores and Other Microorganisms of Clinical Interest, Applied and Environmental Microbiology, 2012, pp. 5077-5082, vol. 78, No. 15.
Korachi, May et al., Low temperature atmospheric plasma for microbial decontamination, FORMATEX, 2013, pp. 453-459.
Kowalski, W.J. et al., Bactericidal Effects of High Airborne Ozone Concentrations on *Escherichia coli* and *Staphylococcus aureus*, Ozone Science and Engineering, 1998, pp. 205-221, vol. 20.
Kvam, Erik et al., Nonthermal Atmospheric Plasma Rapidly Disinfects Multidrug-Resistant Microbes by Inducing Cell Surface Damage, Antimicrobial Agents and Chemotherapy, 2012, pp. 2028-2036, vol. 56, No. 4.
Laroussi, Mounir, Plasma Medicine: Low Temperature Plasma as a Transformational Technology for the Healthcare Field, Laser & Plasma Engineering Institute Old Dominion University, 2012.
Laroussi, Mounir, Plasma-Based Sterilization, Electrical & Computer Engineering Department Old Dominion University, pp. 11-12.
Laroussi, Mounir, Temperature Plasmas for Medicine?, IEEE Transactions on Plasma Science, 2009, pp. 714-725, vol. 37, No. 6.
Li, Yang-Fang, Optimizing the distance for bacterial treatment using surface micro-discharge plasma, New Journal of Physics, 2012, pp. 1-11, vol. 14.
Liang, Yongdong et al., Rapid Inactivation of Biological Species in the Air using Atmospheric Pressure Nonthermal Plasma, American Chemical Society, 2012, pp. A-I.
Maslennikov, Oleg et al., Ozone Therapy in Practice, Health Manual, Ministry of Health Service of the Russian Federation the State Medical Academy of Nizhny Novgorod, 2008, pp. 1-48, Russia.
McDonnell, Kevin et al., Evaluation of the sensitivity of bacterial and yeast cells to cold atmospheric plasma jet treatments, Biointerphases, 2015, pp. 1-9, vol. 10, No. 2.
McTaggart, Lynne, The Quest for the Secret Force of the Universe, Harper Collins Publishers, 2001, pp. 1-289.
Metelmann, Hans-Robert, Head and neck cancer treatment and physical plasma, Clinical Plasma Medicine, 2015, pp. 17-23, vol. 3.
Mikikian, M. et al., Book of Abstracts, 4th International Conference on Plasma Medicine, 2012, Presented in Orleans France.
Misra, N.N. et al., Applications of cold plasma technology in food packaging, Trends in Food Science and Technology, Jan. 2014, pp. 5-17, vol. 35.
Mogul, Rakesh et al., Biomolecular Effects of Cold Plasma Exposure, Astrobiology Technolgy Branch, NASA.
Navya Mastanaiah, Effect of Dielectric and Liquid on Plasma Sterilization Using Dielectric Barrier Discharge Plasma.
Absolute Ozone, Certification of Ozone in USA Food Industries.
Fact Sheet on the Guidelines for Limiting-Exposure to Electric Fields Induced by Movement of the Human Body in a Static Magnetic Field and by Time-Varying Magnetic Fields, Health.
Laser Partners of Oklahoma, Fungi-X.
WHO, Health care-associated infections Fact Sheet, World Health Organization.
ICNIRP, ICNIRP Guidelines for Limiting Exposure to Electric Fields Induced by Movement of the Human Body in a Static Magnetic Field and by Time-Varying Magnetic Fields Below 1 HZ, Health.
LifeVantage, LifeVantage, TrueScience with enchanced Nrf2 technologies Presentation.
Ozone Conversion Units, Physical Properties, Standard conditions.
EPA, Ozone, EPA Guidance Manual Alternative Disinfectants and Oxidants, Apr. 1999, pp. 1-52, vol. 3, No. 1.
Max Planck Institute, Plasma Health Care, A project initiated by the Max Planck Institute for Extraterrestrial Physics.
Drexel, Plasma Medicine: Physical and Biological Mechanisms of Plasma Interaction with Living Tissue Presentation.
Max Planck Institute, Plasma Medicine: Sterilisation and Improved Wound Healing, Max-Planck-Innovation Presentation.
Max Planck Institute, Terraplasma GmbH Flyer, Max Planck Society.
Electroherbalism, The Consolidated Annotated Frequency List (CAFL), The Electroherbalism Frequency Lists, Third Edition, www.electroherbalism.com.
Typical Dosage and Reaction Times to kill bacteria with Ozone.
BC Hydro, Understanding Electric and Magnetic Fields, BC Hydro.
Oryan, Ahmad et al., Bone regenerative medicine: classic options, novel strategies, and future directions, Journal of Orthopaedic Surgery and Research, 2014, pp. 1-27, vol. 9, No. 18.
Palou, Lluis et al., Effects of continuous 0.3 ppm ozone exposure on decay development and physiological responses of peaches and table grapes in cold storage, Postharvest Biology and Technology, 2002.
Pan, Jie et al., A Novel Method of Tooth Whitening Using Cold Plasma Microjet Driven by Direct Current in Atmospheric-Pressure Air,Transactions on Plasma Science, 2010, pp. 3143-3151, vol. 38, No. 11.
Papana, Angeliki et al., Detecting causality in non-stationary time series using Partial Symbolic Transfer Entropy: Evidence in nancial data.
Pournaseh, Yasaman et al, Cold atmospheric plasma jet against Leishmania major in vitro study, Basic Research Journal of Medicine and Clinical Sciences, 2014, pp. 90-94, vol. 4, No. 3.
Ren, Y.X. et al., Mutation Induction by DBD Plasma in Phosphate-solubilizing Bacteria Enterobacter Agglomerans, Energy Procedia, 2012, pp. 211-216, vol. 16.
Rice, Rip et al., U.S. FDA Regulatory Approval of Ozone as an Antimicrobial Agent—What Is Allowed and What Needs to Be Understood, RICE International Consulting Enterprises, pp. 1-13.
Rosani, Umberto et al., Atmospheric-Pressure Cold Plasma Induces Transcriptional Changes in Ex Vivo Human Corneas, PLoS One, 2015, pp. 1-17.
Rutala, William et al., Guideline for Disinfection and Sterilization in Healthcare Facilities, Infection Control Practices Advisory Committee (HICPAC), 2008.
Sarghini, Fabrizio, Cold Plasma Technology: Applications in Food Industry, DIIAT—University of Naples Federico II, Italy.
Sarghini, Fabrizio, Cold PlasmaTechnology: Applications in Food Industy, DIIAT—University of Naples Federico II, Italy.
Shimizu, T et al., Atmospheric Plasma in Medicine: Chronic Wound Disinfection, Applied and Environmental Microbiology.
Shimizu, T et al., The dynamics of ozone generation and mode transition in air surface micro-discharge plasma at atmospheric pressure, New Journal of Physics, 2012, pp. 1-11, vol. 14.
Sivitz, William et al., Mitochondrial Dysfunction in Diabetes: From Molecular Mechanisms to Functional Significance and Therapeutic Opportunities, Antioxidants & Redox Signaling, 2010, pp. 537-577, vol. 12.
Sprey, Karen, Cold plasma therapy could provide an alternative to antibiotics, Dec. 21, 2010, pp. 1-2.
Sun, Peter et al., Atmospheric pressure cold plasma as an antifungal therapy, Applied Physics Letters, American Institute of Physics, 2011, pp. 1-3, vol. 98.

(56) References Cited

OTHER PUBLICATIONS

Svarcova, Michaela et al., Treatment of a Superficial Mycosis by Low-temperature Plasma: A Case Report, Prague Medical Report, 2014, pp. 73-78, vol. 115, No. 1.

Virard, Francois et al., Cold Atmospheric Plasma Induces a Predominantly Necrotic Cell Death via the Microenvironment, PoLS One, 2015, pp. 1-16.

Wang, Mian et al., Cold Atmospheric Plasma for Selectively Ablating Metastatic Breast Cancer Cells, PLOS One, Sep. 2013, pp. 1-11, vol. 8, No. 9.

Weiss, Martin et al., Cold Atmospheric Plasma Treatment Induces Anti-Proliferative Effects in Prostate Cancer Cells by Redox and Apoptotic Signaling Pathways, PLoS One, 2015, pp. 1-17.

Wikol, Michael et al., Expanded Polytetratluoroethylene Membranes and Their Applications, Filtration and Purification in the Biopharmaceutical Industry, Second Edition, pp. 619-640.

Wu, Yan et al., MS2 Virus Inactivation by Atmospheric-Pressure Cold Plasma Using Different Gas Carriers and Power Levels, Applied and Environmental Microbiology, 2015, pp. 996-1002, vol. 81 No. 3.

Yoshinari, Masao et al., Surface modification by cold-plasma technique for dental implants—Bio-functionalization with binding pharmaceuticals, Japanese Dental Science Review, 2011, pp. 89-101.

Zhang, Hao, Effects and Mechanism of Atmospheric-Pressure Dielectric Barrier Discharge Cold Plasma on Lactate Dehydrogenase (LDH) Enzymet, Scientific Reports, 2015, pp. 1-12, vol. 5, No. 10031.

Zhu, Wei et al., Cold Atmospheric Plasma Modified Electrospun Scaffolds with Embedded Microspheres for Improved Cartilage Regeneration, PoLS One, 2015, pp. 1-18.

Zimmermann, Julia et al., In vivo skin treatment using two portable plasma devices: Comparison of a direct and an indirect cold atmospheric plasma treatment, Clinical Plasma Medicine, 2013, pp. 35-49, vol. 1.

\* cited by examiner

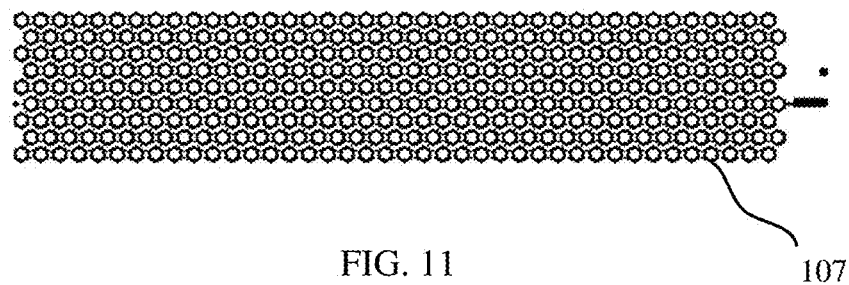
FIG. 11         107
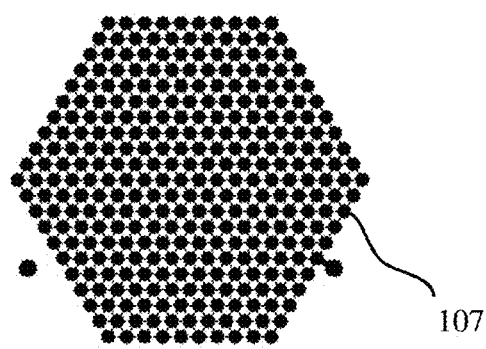
107
FIG. 12
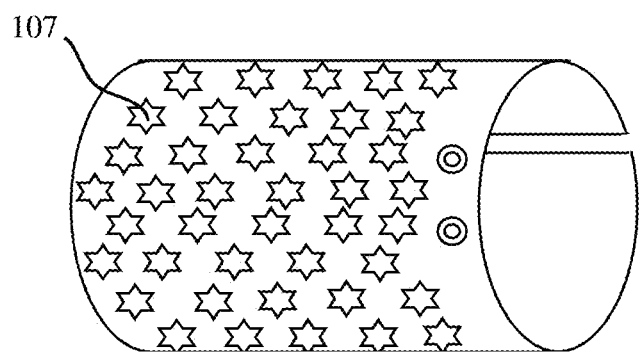
FIG. 13

DEVICES FOR CONTROLLING NON-THERMAL PLASMA EMITTERS

CROSS-REFERENCE TO RELATED APPLICATIONS

This application claims the benefit of U.S. Provisional Application No. 62/235,517 filed Sep. 30, 2015 and is a continuation-in-part of co-pending U.S. patent application Ser. No. 15/055,028 filed Feb. 26, 2016. Both aforementioned applications are incorporated by reference herein in their entirety.

FIELD OF INVENTION

The present invention relates to a device used to drive non-thermal plasma emitters and control the emitted plasma for use in plasma medicine including therapeutic and diagnostic applications.

BACKGROUND

Plasma is an ionized state of matter known for its cleaning, decontaminating, sterilizing, antimicrobial and healing properties when applied to an inanimate surface or to tissue. Plasma can be created when energy is applied to a substance. As energy input is increased the state of matter changes from solid, to liquid, to a gaseous state. If additional energy is fed into the gaseous state, the atoms or molecules in the gas will ionize and change into the energy-rich plasma state, or the fourth fundamental state of matter.

There are two types of plasma, thermal and non-thermal, which is also known as cold plasma. Thermal plasmas are in thermal equilibrium, i.e. the electrons and the heavy particles are at the same temperature. Current technologies create thermal plasma by heating gas or subjecting the gas to a strong electromagnetic field applied with a generator. As energy is applied with heat or electromagnetic field, the number of electrons can either decrease or increase, creating positively or negatively charged particles called ions. Thermal plasma can be produced by plasma torches or in high-pressure discharges. If thermal plasma is used in treating a material or surface sensitive to heat, it can cause significant thermal desiccation, burning, scarring and other damage.

In order to mitigate such damage, methods and devices have been created for applying non-thermal plasma to heat-sensitive materials and surfaces. Whereas in thermal plasmas the heavy particles and electrons are in thermal equilibrium with each other, in non-thermal plasmas the ions and neutrals are at a much lower temperature (sometimes as low as room temperature) than the electrons. Non-thermal plasma usually can operate at less than 104° F. at the point of contact. Thus non-thermal plasmas are not likely to damage human tissue.

To create non-thermal plasma, a potential gradient is applied between two electrodes. Typically the electrodes are in an environment of a fluid such as helium, nitrogen, heliox, argon, or air. When the potential gradient between the high voltage electrode and grounded electrode is large enough, the fluid between the electrodes ionizes and becomes conductive. For example, in the plasma pencil a dielectric tube contains two disk-shaped electrodes of about the same diameter as the tube, separated by a small gap. The disks are perforated. High voltage is applied between the two electrodes and a gas mixture, such as helium and oxygen, is flowed through the holes of the electrodes. When the potential gradient is large enough, a plasma is ignited in the gap between the electrodes and a plasma plume reaching lengths up to 12 cm is discharged through the aperture of the outer electrode and into the surrounding room air. The plume can be used to treat surfaces by scanning it across the surface.

Plasma systems requiring forced gas can be very large and cumbersome, requiring the use of gas tanks to supply the necessary fluid to create the plasma. Another disadvantage is that there is only a narrow contact point between the plasma plume and the surface that it comes into contact with. Typically, plumes are usually on the order of 1 cm in diameter. This makes treating larger areas time-consuming and tedious, since the contact point has to be moved back and forth across the area to be treated. The uniformity of treatment across the treatment area may be difficult to control.

Another commonly used method for creating non-thermal plasma is the dielectric barrier discharge ("DBD"), which is the electrical discharge resulting after high voltage is applied between two electrodes separated by an insulating dielectric barrier. DBD is a practical method of generating non-thermal plasma from air at ambient temperature and comes in several variants. For example, a volume dielectric barrier discharge ("VDBD") occurs between two similar electrodes with a dielectric barrier on one electrode, and the electrodes facing each other. A VDBD is limited by the space between the two electrodes, the size of the electrodes, and cannot conform to different surface topographies. A surface dielectric barrier discharge ("SDBD") can occur between one electrode and a surface such as skin, metal, or plastic. In a specific example of SDBD, known as a floating electrode dielectric barrier discharge ("FE-DBD") variation, one of the electrodes is protected by a dielectric such as quartz and the second electrode is a human or animal skin or organ. In the FE-DBD setup, the second electrode is not grounded and remains at a floating potential. A SDBD treatment area is limited by the electrodes' size, and like the VDBD, it cannot conform to the surface the electrode comes into contact with. In current SDBD technologies there is only a single contact point between the plasma plume and the surface that it comes into contact with.

Another type of non-thermal plasma is known as corona discharge, which is an electrical discharge brought on by the ionization of a fluid surrounding a conductor that is electrically charged. Corona discharges occurs at relatively high-pressures, including atmospheric pressure, in regions of sharply non-uniform electric fields. The field near one or both electrodes must be stronger than the rest of the fluid. This occurs at sharp points, edges or small diameter wires. The corona occurs when the potential gradient of the electric field around the conductor is high enough to form a conductive region in the fluid, but not high enough to cause electrical breakdown or arcing to nearby objects. The ionized gas of a corona is chemically active. In air, this generates gases such as ozone ($O_3$) and nitric oxide (NO), and in turn nitric dioxide ($NO_2$). Ozone is intentionally created this way in an ozone generator, but otherwise these highly corrosive substances are typically objectionable because they are highly reactive. It would be desirable to take advantage of the reactive nature of these gas molecules.

Beyond generating the non-thermal plasma, it would be desirable to be able to control the plasma so that it can be used for beneficial purposes. It would be desirable to control the length of time the plasma is generated, the power level of the plasma, and to modulate the frequency and wave form of the plasma. Specific modulation frequencies are correlated to the killing of specific microorganisms, including forms of bacteria, virus, fungus, and mold. Therefore it would be desirable to be able to control such pulse frequency of the plasma too. In this way a plasma can be used to produce biological effects beyond those produced by the reactive species. To ensure the emitted plasma meets desired parameters, it would be useful to limit the emissions to the desired parameters and by authorized persons. It would also be desirable that such a controller be portable and battery powered for convenience. It would also be desirable that the controller be usable for multiple sizes and shapes of plasma generators.

Therefore, it is an object of this invention to provide a device that drives non-thermal plasma emitters and controls the emitted plasma for use in plasma medicine.

SUMMARY

This device is a power supply that drives and controls an array of non-thermal plasma emitters at desired frequencies and at a controlled power level. It creates a high voltage at a high frequency. The power supply is connected to the array with a micro-coaxial cable. The power supply comprises a step-up transformer, a balanced driver, and a controller. The power supply is designed such that the transformer operates at the resonant frequency of the combined capacitance of the array and connecting cable. The power source is preferably a battery and the power into the array is monitored by the controller and can be adjusted by the user.

In one embodiment the balanced driver is driven directly by the controller. The controller monitors the phase relationship between the transformer primary winding voltage and the gate drive voltage, and adjusts the drive frequency to resonance. In another embodiment the balanced driver is configured as an oscillator, which drives the transformer at resonance by default. A signal from the transformer driver generates an interrupt to the controller for synchronizing current and voltage measurements for power control.

BRIEF DESCRIPTION OF DRAWINGS

FIG. 11 is a top view of a fifth embodiment of a non-thermal plasma array of the present invention in which the plasma emitters are in a rectangular arrangement.

FIG. 12 is a top view of a sixth embodiment of a non-thermal plasma array of the present invention in which the plasma emitters are in a hexagonal arrangement.

FIG. 13 is a perspective view of a seventh embodiment illustrating a non-thermal plasma array as a tube.

DETAILED DESCRIPTION

An array 100 comprises a plurality of non-thermal plasma emitters 107, disposed on a rigid or flexible substrate. The emitters 107 are arranged such that when the array 100 is connected to a voltage source the emitters generate a plurality of corona discharges. The discharges generate ionized gas, which in turn creates reactive species including ozone and nitric oxide.

Figure 1:
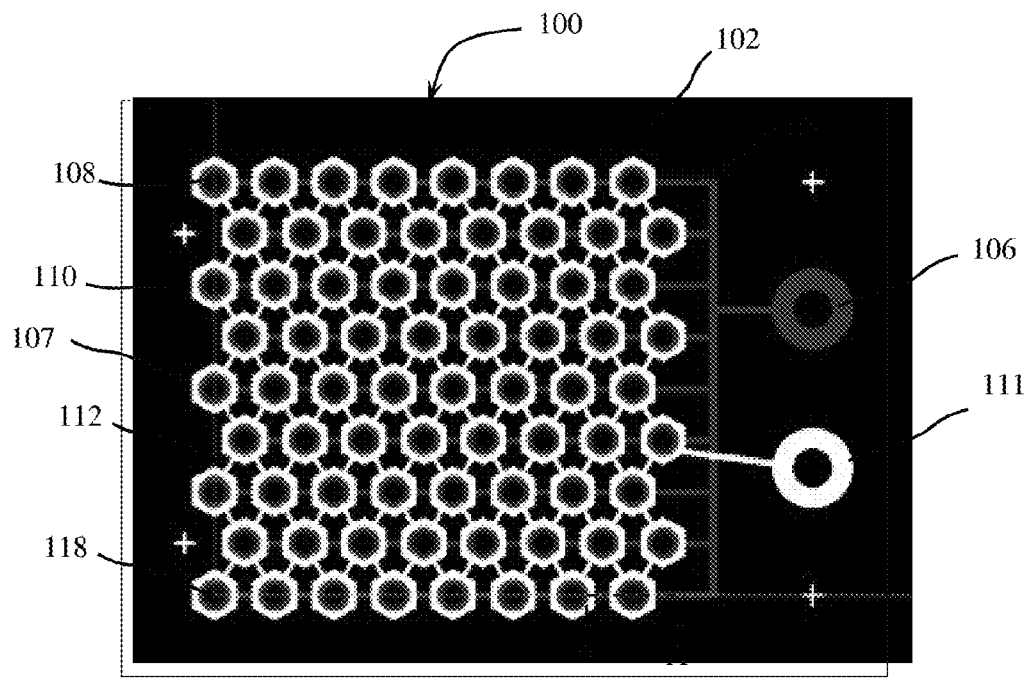
FIG. 1 is a top view of a first embodiment of an array of non-thermal plasma emitters.
Figure 2:
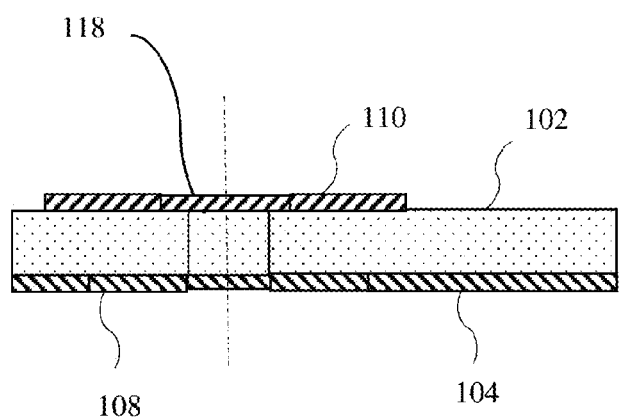
FIG. 2 is a cross-sectional view of a plasma emitter along line A-A of FIG. 1.
Figure 3:
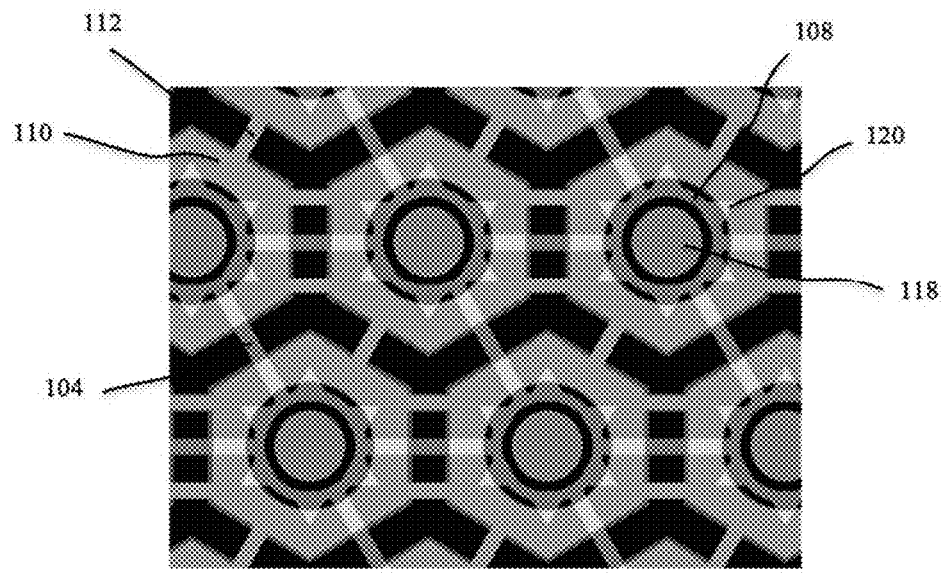
FIG. 3 is a partial top view of a second embodiment of a non-thermal plasma emitters.

Referring initially to FIG. 1, a non-thermal plasma array is shown generally at 100. The array comprises a substrate 102 having at least two opposing surfaces, referred to herein sometimes as a top and bottom for convenience. A plurality of through-holes 118 is made in the substrate 102. A plurality of drive electrodes 110 is placed on the top of the substrate 102, with each drive electrode 110 centered over one through-hole 118 in the substrate 102. A plurality of ground electrodes 108 is placed on the bottom of the substrate 102, with each ground electrode 108 centered over one through-hole 118 in the substrate 102. The resulting structure of a through-hole, a ground electrode, and a drive electrode comprises a plasma emitter 107. FIG. 2 shows a cross-sectional view of a plasma emitter with through-holes. Each drive electrode 110 and ground electrode 108 is generally centered on a through-hole 118, but in certain embodiments it may be off-center. Each electrode's 110 shape is preferably symmetric around the through-hole 118, such as a hexagon, circle, triangle, rectangle, square, or other shape, but in certain embodiments can be asymmetric. FIGS. 1 and 3 illustrate an embodiment in which the drive electrode 110 is hexagonal.

Figure 4:
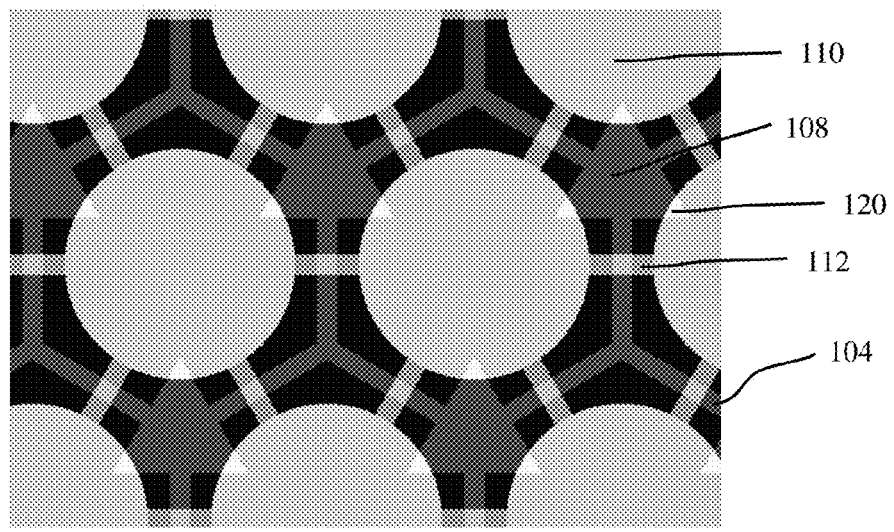
FIG. 4 is a partial top view of a third embodiment of a non-thermal plasma emitters without through-holes in the substrate.

FIG. 4 shows another embodiment of a non-thermal and ozone plasma array 200 wherein a substrate does not have through-holes. Here a plurality of drive electrodes 110 is placed on the top of the substrate 102, with each drive electrode 110 centered over a ground electrode 108 on the bottom of the substrate 102. The resulting structure of a drive electrode on a dielectric substrate over a ground electrode is also referred to herein as a plasma emitter 107.

A conductive drive track 112 on the top of the substrate 102 is connected to at least one drive electrode 110. A conductive ground track 104 on the bottom of the substrate 102 is connected to at least one ground electrode 108. One or more drive tracks 112 may be used to interconnect as many drive electrodes 110 together as desired. Similarly, one or more ground tracks 104 may be used to interconnect as many ground electrodes 108 together as desired. Emitters may be connected in series or in parallel, and preferably in parallel for a lower driving voltage.

A drive terminal 111 is connected to the drive track 112 and a ground terminal 106 is connected to the ground track 104. The drive electrodes 110 are interconnected and connected to a drive terminal 111. Similarly, the ground electrodes are interconnected and connected to a ground terminal 106. The resultant structure is much like a printed circuit board.

The substrate 102 is made of a dielectric material such as alumina, polycarbonate, polyimide, polyester, polytetrafluoroethylene-infused woven glass cloth, polypropylene, glass-reinforced epoxy laminate sheets, or the like. In certain embodiments a substrate has more than one layer, and the layers may be made of different materials. The substrate 102 is made of a rigid or a flexible material that can be made to conform to varying surface topography and shapes such as a rough surface, a textured surface, a smooth surface. The substrate can be two-dimensional, such as a square, curved, rectangular, round, or hexagonal. It can also be three-dimensional such as curved, cubic, tubular, or spherical.

The substrate may also have a non-uniform shape or a non-symmetric shape. Substrates of rigid materials may be shaped to the desired conformation before or after the plasma emitters are made therein. Substrates of flexible materials are typically conformed to the desired shape after the array is manufactured.

In a preferred embodiment, the substrate is made of thin FR-4. At a thickness of about 0.2 mm, the substrate made of FR-4 is somewhat flexible. As an alternative, the array can be fabricated from more flexible material such as polyimide film or PTFE infused fiberglass.

Using mass manufacturing techniques, the cost of making the arrays is small enough that the arrays can be considered consumable or disposable, simply thrown away or recycled after one or a few uses. Any polymer in the array is consumed by the oxygen plasma, in a process commonly known as ashing. This erosion process can be slowed by adding a thin layer of glass on top of the entire array. A sol-gel process can be used to deposit thick layer, on the order of about a 100 nm. A thinner crystalline layer of $SiO_2$, $Al_2O_3$ or $Y_2O_3$ works too, and may be deposited by atomic layer deposition or plasma assisted atomic layer deposition, optionally after array burn-in for uniform plasma.

A through-hole 118 helps reduce the array capacitance and is a ventilation hole for a fluid to flow from a drive electrode 110 to a ground electrode 108. Such fluids include oxygen, helium, nitrogen, sulfur hexafluoride, carbon dioxide, air, and other gases. In the preferred embodiment, the fluid is air at ambient pressure, about 1 atmosphere. The oxygen in the air is ionized by the plasma generated by the emitters 107, creating ozone. The through-holes 118 are made by drilling, etching, cutting, laser cutting, punching, or other method. In certain embodiments a through-hole is lined with a structure that directs the fluid to each electrode such as a pipe, tube, channel, or the like. A through-hole 118 can be circular, rectangular, triangular, trapezoidal, hexagonal, or other shape.

A drive electrode 110 is capacitively coupled to ground electrode 108 at a point or points where the ground electrode touches the drive electrode such that when a high-enough voltage is applied to a drive electrode 110, the surrounding fluid is ionized and a plasma is created, causing electrons to flow between the drive and ground electrode.

Figure 15A:
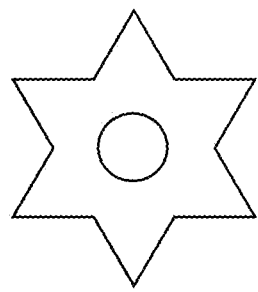
FIGS. 15A-D illustrate ground electrodes having points of various shapes.
Figure 15B:
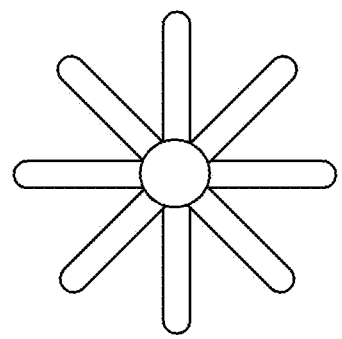
Figure 15C:
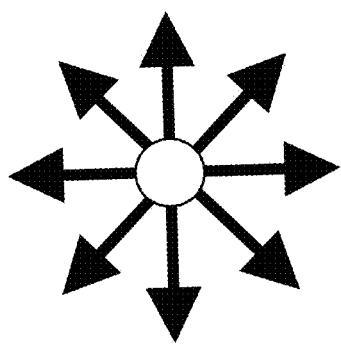
Figure 15D:
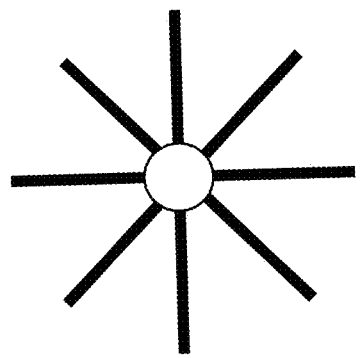

It is desirable to have a sharp point where the plasma is generated, since this is used to help initiate the plasma. The sharp points may take any form, such as a sharp point, a blunt point, a spear point a radius, or the like. FIG. 3 illustrates an embodiment in which the ground electrode 108 is a star with six sharp points 120. FIG. 4 illustrates an embodiment in which the ground electrode 108 is a triangle with three sharp points 120. FIG. 15A illustrates an electrode with six sharp points; FIG. 15B shows blunt points; FIG. 15C shows spear points; and FIG. 15D shows radius points.

A drive electrode 110, drive track 112, ground electrode 108 and a ground track 104 can be printed, etched, laminated, or otherwise disposed onto the substrate 102. They can be made of copper, silver, nickel, or any other conductive material. The can be insulated, such as by a solder mask, polyester film such as Mylar®, mica, polypropylene, polytetrafluoroethylene such as Teflon®, or the like, and in other embodiments are not insulated. For manufacturing convenience, preferably the drive electrode 110 and ground drive 112 are made of the same material and disposed onto the substrate 102 at the same time. Similarly, preferably the ground electrode 108 and ground track 104 are made of the same material and disposed onto the substrate 102 at the same time. Alternatively the drive electrode 110, drive track 112, ground electrode 108 and a ground track 104 are made of different materials and may be disposed on the substrate in processes occurring at the same or different times.

Figure 5:
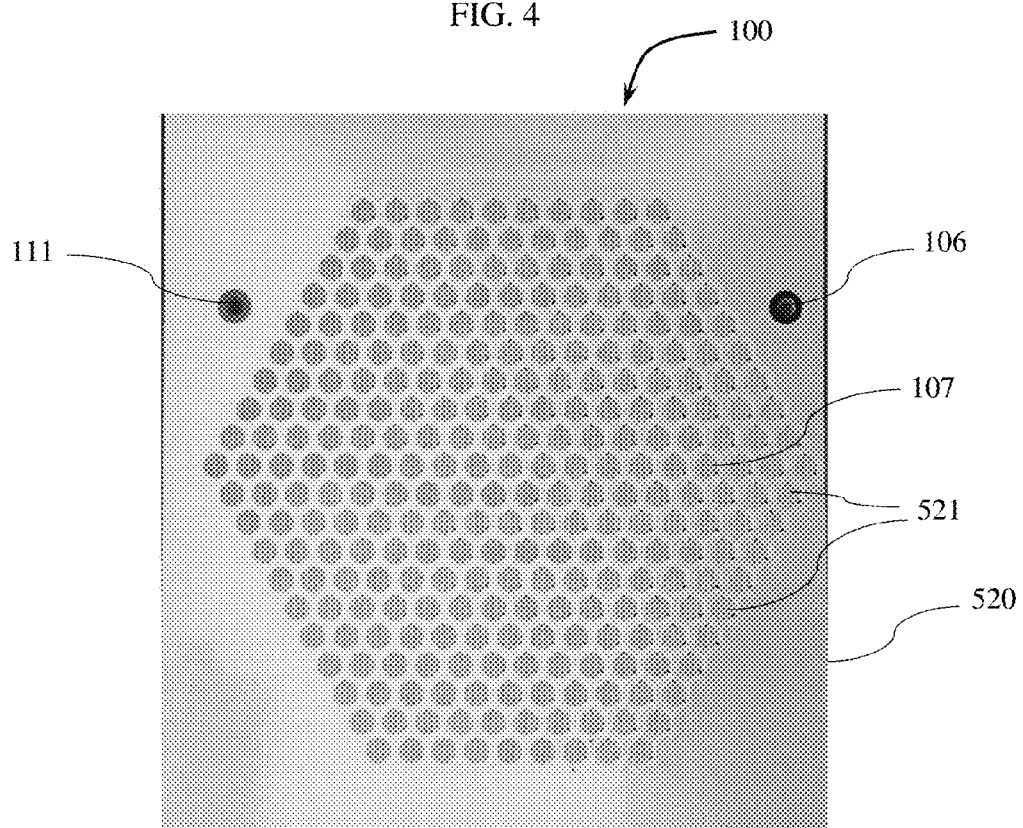
FIG. 5 is a top view of a fourth embodiment of an array with a woven array of plasma emitters.
Figure 6:
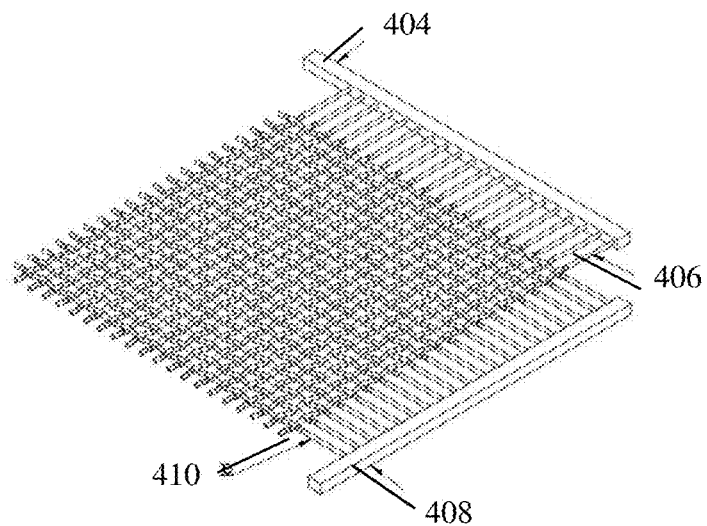
FIG. 6 is a schematic illustrating in perspective a portion of the woven array of FIG. 5.

FIGS. 5 and 6 show another embodiment of a non-thermal array 100 wherein a plurality of plasma emitters 107 is created at the intersections of wires that are woven together. The wires 410 of drive electrode 408 are woven with the wires 406 of ground electrode 404 to form a woven array. One electrode is connected to a plurality of insulated wires and the other connected to a plurality of uninsulated wires. If the wire insulation is a polymer, a coating, such as $SiO_2$, is preferred to prevent ashing. The air in the interstitial space between the wires is ignited to form a plasma. Wires can be copper, silver, nickel, or any other conductive material. The wires are insulated with non-conductive or dielectric materials such as plastic, rubber-like polymers, or varnish. In FIG. 5 the emitters 107 are covered by a rigid sheath 520 having hexagonal apertures 521.

The drive terminal 111 and ground terminal 106 are printed, cut, punched, laminated, etched, connected, or otherwise attached to the drive track 112 and ground track 104, respectively. There are at least those two terminals for each array of emitters, but there may be as many terminals as desired. For example, there may be two terminals for each emitter 107, or there may be more than two terminals for each emitter 107, for example if extra terminals are desired for redundancy in case of failure, or to have better placement for connection to the voltage source. Preferably the terminals 111 and 106 are attached to or integral with the substrate, such as with solder pads, banana plugs, ring terminals, spade terminals, pin terminals, or the like.

The emitters 107 can be arranged in a variety of relative positions, such as lines, concentric circles, random placement, etc. The arrangement of emitters is sometimes referred to herein as an array. An array can take on any shape to fit the user's needs. Typically the arrangement of the emitters 107 is generally symmetrical, such as a rectangle or hexagon, but the arrangement can be non-symmetrical too, which can be useful for using a single substrate target separate areas with different concentrations of plasma. FIG. 1 illustrates the emitters 107 arranged in rows, and each row is offset from the previous row. This same pattern is repeated with as many rows as the user needs to form the desired size of the array. The rows illustrated in FIG. 1 have 8 emitters each, but any number of emitters can be used in each row. The rows illustrated in FIG. 7 have 8 emitters each, but any number of emitters can be used in each row.

Figure 14:
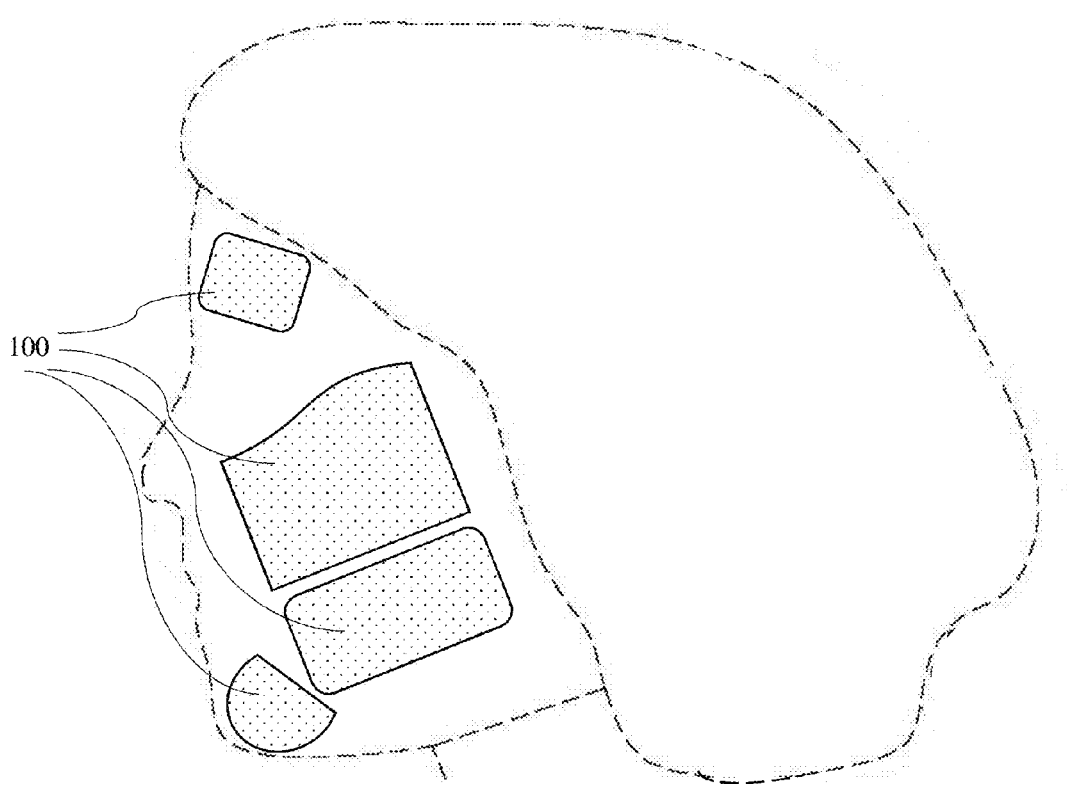
FIG. 14 illustrates plasma arrays used to treat a patient's face in which several smaller arrays are connected to each other to effectively create a larger area of plasma discharge.

The size of the array ranges from microscopic to macroscopic and, while theoretically unlimited, in practice is limited by manufacturing techniques. In practice, the arrays are typically less than 5 inches in any dimension. If a larger area of plasma discharge is desired, smaller arrays can be placed side-by-side and connected to each other to effectively create a larger array controlled as a single array. FIG. 14 illustrates plasma arrays 100 used to treat a patient's face in which several smaller arrays are connected to each other to effectively create a larger area of plasma discharge. In other cases, the smaller arrays are placed sized-by-side to create a larger array, but are not connected to each other so that they can be controlled independently.

Plasmas can be defined in a number of characteristics including size (typically in meters), lifetime (seconds), density (particles per cubic meter) and temperature. In certain embodiments a first emitter 107 has a different plasma strength than a second emitter 107. The plasma strength is determined by a number of factors including dielectric thickness, drive voltage (which determines the duty cycle in which the plasma is ignited and retained), and atmospheric pressure. Typically the resultant plasma is fan shaped, extending about 0.8 mm from the point and about 120 degrees of fan.

Figure 7:
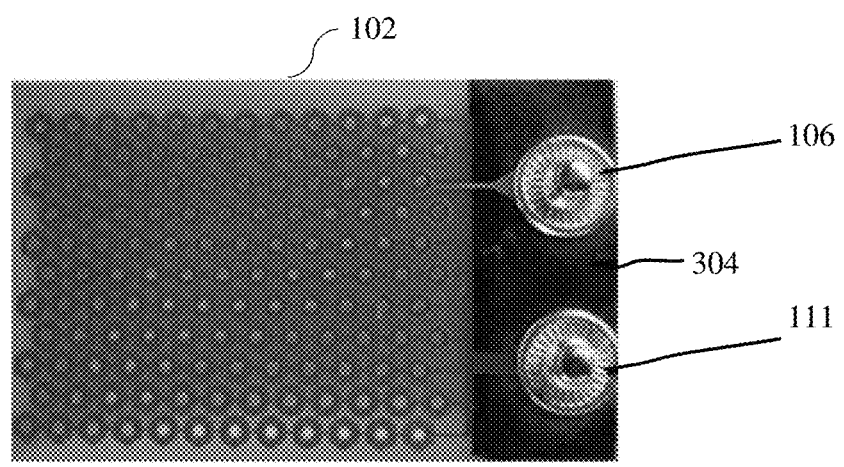
FIG. 7 is a photograph of the first embodiment of an array with a flexible substrate and its terminal connection points.
Figure 8:
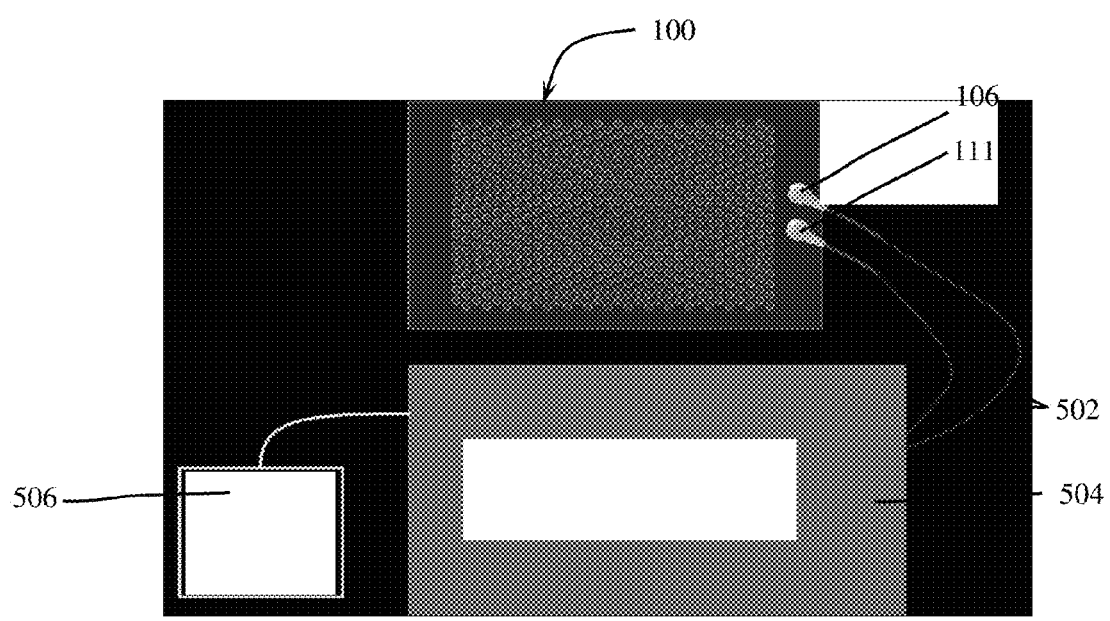
FIG. 8 illustrates a general overview of a non-thermal plasma device with a controller and an external power source.

FIG. 7 shows a non-thermal plasma array 100 in which an insulative layer 304 is attached to the substrate 102, under the ground terminal 106 and driver terminal 111. The insulative layer 304 can be neoprene, polymer coating, Mylar®, Teflon®, or the like.

Figure 9:
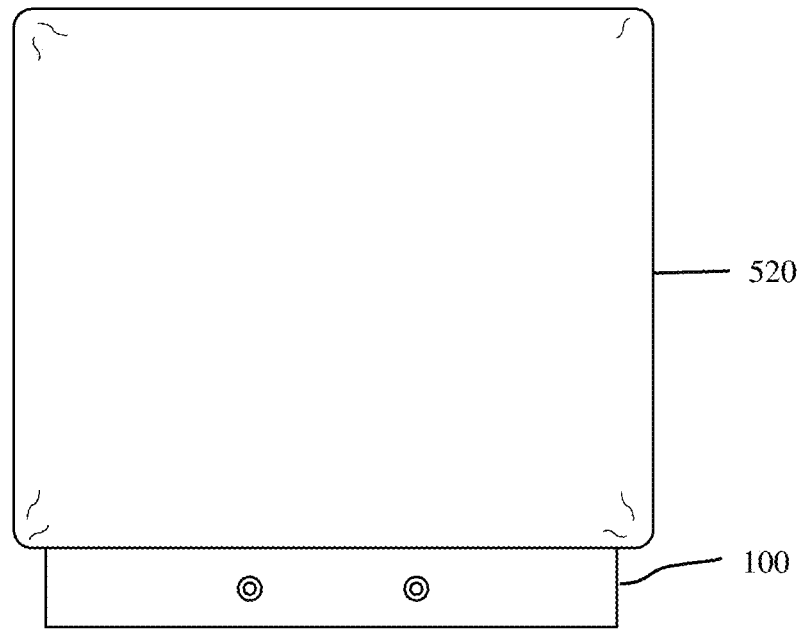
FIG. 9 is a top view of a non-thermal plasma array that is partially covered with a flexible sheath.
Figure 10:
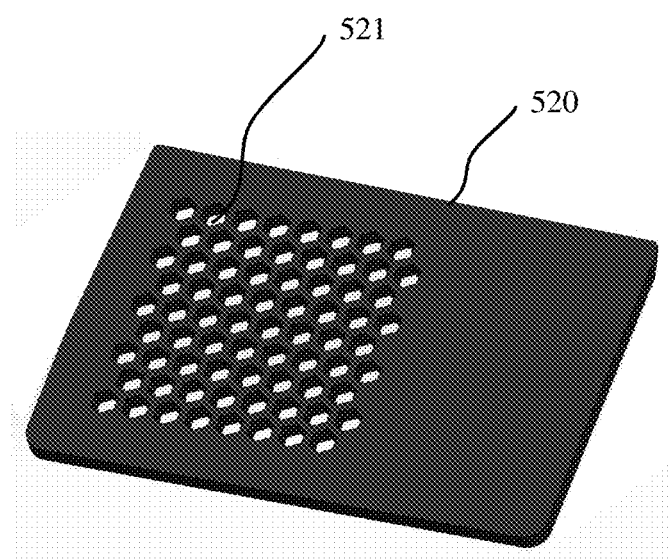
FIG. 10 is a top perspective view of rigid sheath partially covering a non-thermal plasma array.

FIG. 9 shows a non-thermal plasma array 100 with a sheath 520 covering at the plasma emitters. In some embodiments only some of the emitters are covered. In a preferred embodiment the sheath 520 is an electrical insulator that acts as a barrier between the array and a surface of interest. The electrical insulator 520 allows plasma generated from the array to effect and react with a surface of interest, but does not allow fluids to permeate thru the cover to the created plasma, and surface of a substrate. Thus it is breathable to gaseous molecules, protects a user or surface from possible electrical shocks, and prevents liquids from getting to the electrodes that might cause electrical shorts. Preferably the sheath 520 is flexible and made of polytetrafluoroethylene ("PTFE"), which provides a water-resistant yet breathable covering. Flexible sheaths can also be made of expanded polytetrafluoroethylene, neoprene, hydrophobic polyester, hydrophilic polyester, or the like. FIG. 10 shows one embodiment of a rigid sheath 520 with apertures 521 centered on the through-holes 118 that are on the non-thermal plasma array 100. The sheath 520 can vary in length, width, and height to fit a non-thermal plasma array's size and shape. Typically the sheath is also removable.

A non-thermal plasma array 100 can conform to any shape or size, size for treating human diseases in various anatomical locations such as a toe, ear, finger, face, etc.

FIGS. 11, 12 and 13 show examples of additional embodiments of the array 100. FIG. 11 shows a rectangular array 100 of plasma emitters 107 in which one side of the array is substantially longer than the other side. This arrangement may be particularly useful for the treatment of large narrow surface areas. FIG. 12 shows a hexagonal array 100 of plasma emitters 107. FIG. 13 shows an array 100 formed into a tube, with plasma emitters arranged along the surface of the tube. This arrangement may be particularly useful for the treatment of tubular-shaped areas such as fingers so that the inside of the tube stays in contact with the outside of the finger. This arrangement may also be particularly useful for treating the inside surface of a tubular human body part such as an ear canal in which the outside of the tube stays in contact with the inner surface of the ear canal. The tubular array 100 can be pre-formed on a rigid or flexible substrate. Alternatively, a rectangular array 100 on a flexible substrate can be bent into a tube at the time of treatment.

To create the plasma, a voltage is applied to one or more drive electrodes 110 with a power supply 500, sometimes also referred to herein as a driver. It creates a high voltage at a high frequency. With the drive electrodes 110 at a high potential relative to the ground electrode 108, current flows through the drive electrodes 110 and through a fluid in the through-hole 118 and around the array. The fluid is ionized to create a plasma region around each drive electrode 110, ground electrode 108 or both. The ions from the ionized fluid pass a charge to a plurality of ground electrodes 108 or to an area of lower potential. In a preferred embodiment the power supply 500 drives and controls an array 100 of non-thermal plasma emitters at desired frequencies at a controlled power level. The power supply 500 is connected by wire or wirelessly to a controller 204. The controller 204 controls the functionality of the array 100 such as time on/off, strength of plasma, strength of a plasma field from electrode to electrode, frequency, power, and the like. The characteristics of the power supply will depend largely on the size of the array.

Figure 16:
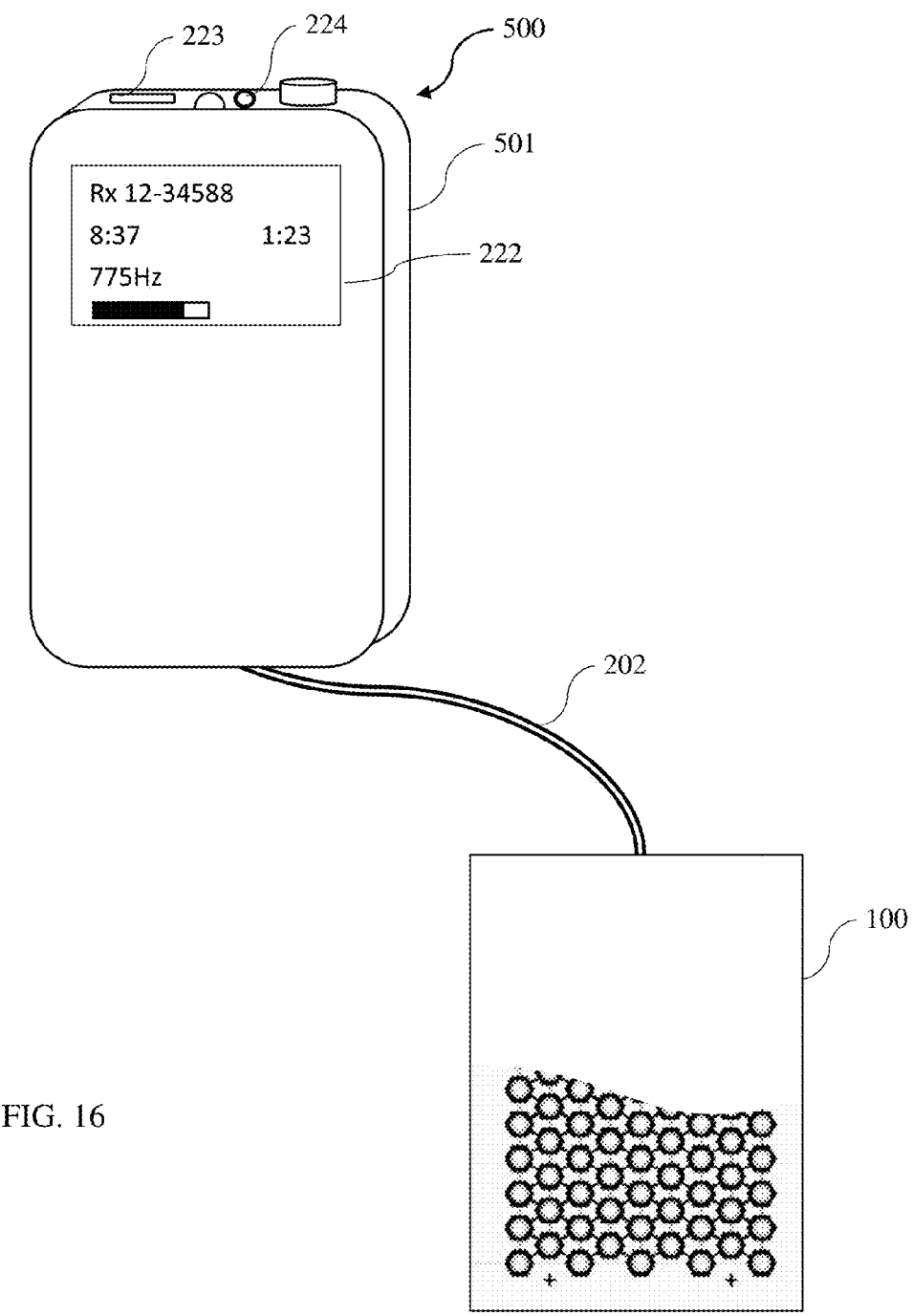
FIG. 16 is a front perspective view of the power supply of the present invention connected to an array of plasma emitters, shown in a partial cut-away view.
Figure 17:
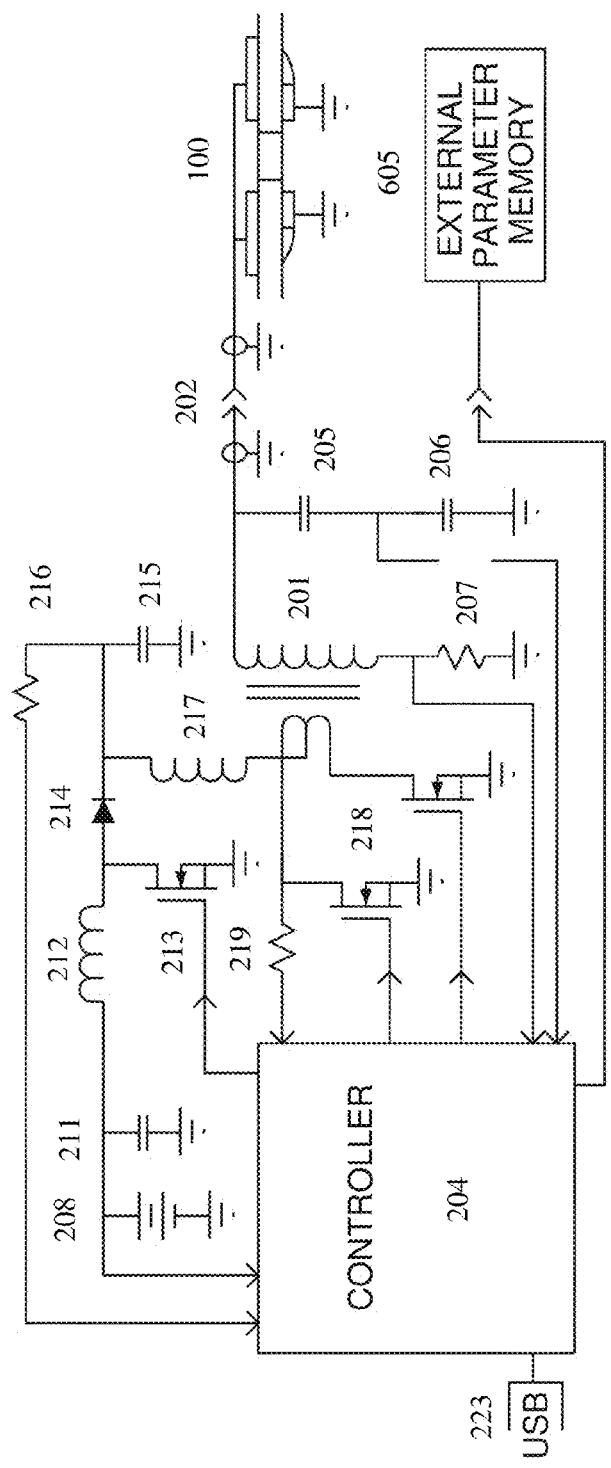
FIG. 17 is a schematic diagram of one embodiment of the proposed power supply.

The power supply 500 is connected to the array 100 with a micro-coaxial cable, leads 502, or other connector, referred to herein generally as a cable 202. See FIG. 16. The power supply 500 comprises a step-up transformer 201, a balanced driver, and a controller 204. See FIG. 17. The power supply 500 further comprises a power source 506, which is preferably a battery. The power into the array is monitored by the controller 204 and can be adjusted by the user.

The inductance of the transformer's secondary winding and the combined capacitance of the array and cable form a parallel LC circuit with a particular resonant frequency. This arrangement takes advantage of the resonance phenomenon that occurs when a vibrating system or external force, such as the power supply 500, drives another system, such as the array 100, to oscillate with greater amplitude at a specific preferential frequency. The modulation frequency could be set manually. However, since the resonant circuit Q factor is relatively high (above 300), so that the range of frequencies the device resonates at is relatively small, an automatic tuning mechanism is preferred for reliable operation. This is done by monitoring the phase relationship between voltage and current on the primary winding to determine when the transformer is operating at resonance. In a preferred embodiment, the drive frequency is in the 100 kHz range to allow a relatively wide range of modulation frequencies. However, the described invention could operate over a very wide range, 10 kHz to over 10 MHz, depending on the driving electronics.

The preferred embodiment will resonate at the combined capacitance of the array 100 and the cable 202 with a tuned step-up transformer to generate high voltage AC at the array 100. The high Q of the tuned circuit produces a clean sinusoidal drive waveform to minimize harmonic radiation and provides a voltage boost. The controller 204 adjusts the transformer drive frequency to the resonant frequency of the tuned circuit. The resultant plasma frequency typically remains steady and is pulsed to create a modulated therapeutic frequency. However, the transformer secondary or primary voltage can also be monitored as the modulation frequency is adjusted, to detect a change in breakdown voltage versus modulation frequency. This may be used to adjust the modulation frequency for maximum therapeutic effect.

The input power used for the array driver is typically DC although the array itself intrinsically requires AC. The power supply 500 converts DC to AC. Typically the plasma frequency will operate at given frequency between about 50-100 kHz. In a preferred embodiment, the AC voltage applied to the drive electrodes is modulated in pulses, typically at a frequency between above 0 Hz to about 10 kHz. Modulation is done by turning this frequency on and off, i.e. generating the modulation digitally by pulse-width modulation of the transformer primary drive waveforms. This could be square wave modulation, or other waveform type such as sine wave. For example, for a plasma frequency of 50 Hz, the array emits periodic bursts of 50 Hz energy. Alternatively a continuous wave voltage is applied to the drive electrodes.

Figure 22:
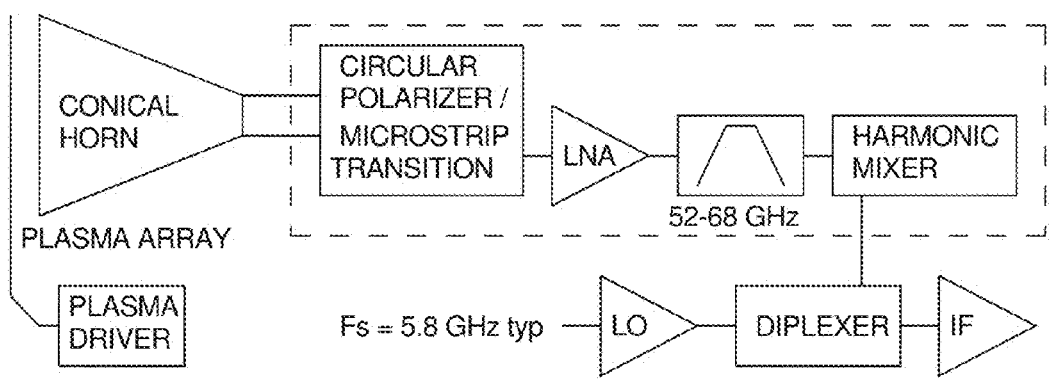
FIG. 22 is a schematic diagram of a circuit for a frequency scan function in the plasma driver.
Figure 23A:
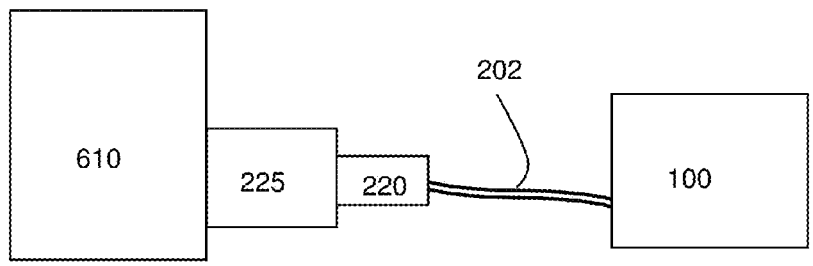
FIGS. 23A-D illustrate alternate arrangements of the driver and the array.
Figure 23B:
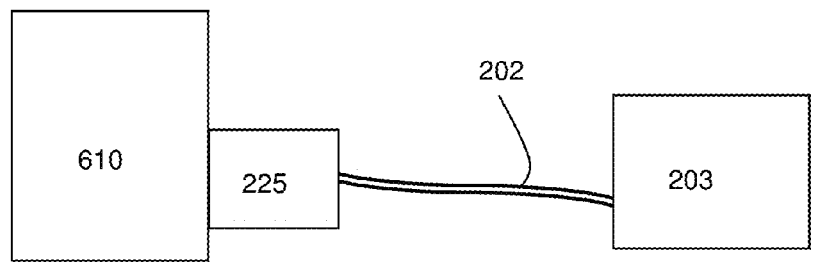
Figure 23C:
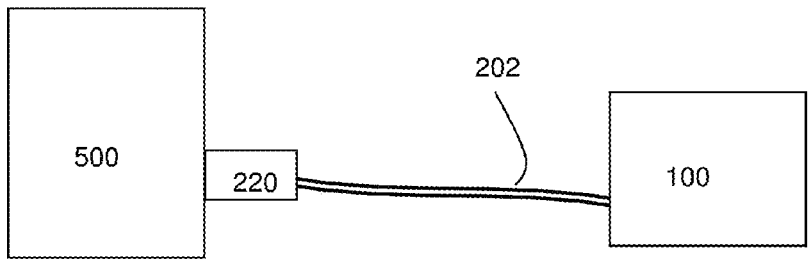
Figure 23D:
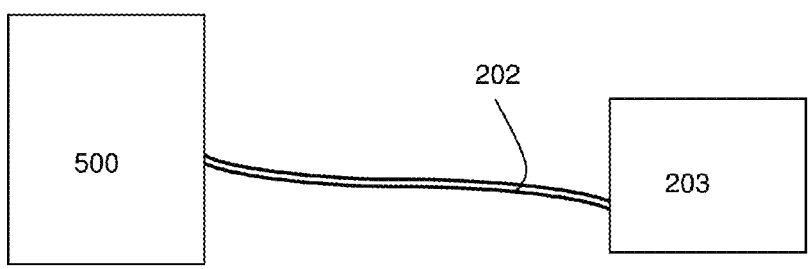

Correlation has been observed between modulation frequency and biological effects. A modulation frequency scan function in the plasma driver can use the relative plasma power measurement to determine the optimal modulation frequency for treating a particular condition, or for measuring the progress of a treatment. To obtain more detailed information between the biological interaction with the plasma array, a search is conducted for radio signals in the range of the oxygen maser mechanism. See FIG. 22.

If a therapeutic plasma frequency is found, the plasma frequency can be adjusted by adding parallel capacitance of an appropriate value. Since the voltage is about 1 kV RMS, this is typically done by switching high voltage capacitors with a relay. A practical solution would typically use a set of seven binary related values. The AC drive voltage can also be modulated if a therapeutic modulation frequency is found. This would typically be done be adjusting timer values in the digital controller in the driver.

A preferred embodiment monitors transformer primary voltage and current, using this data for power control and for hardware interlock to mitigate against catastrophic failure of the electronics. Excessive power will shorten the life of the array. Since the array will eventually fail from erosion of the dielectric, fast current limiting will allow a graceful and safe end of operation.

Figure 18:
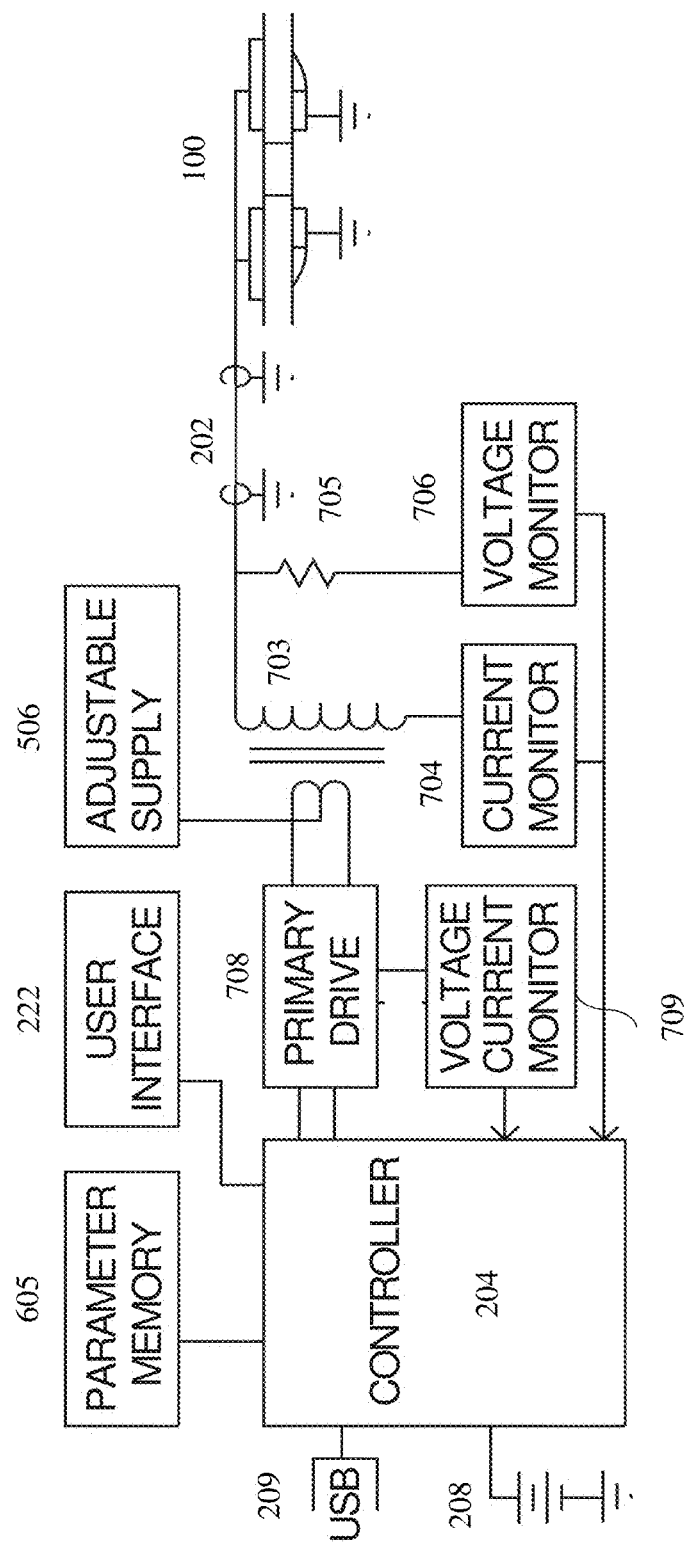
FIG. 18 is a schematic diagram of a second embodiment of the proposed power supply.

FIG. 18 shows a typical system level block diagram. Array 100 is connected to the power supply 500 with cable 202, preferably using a connector (as opposed to hard-wired) so that the cable can be easily removed and reused in the case of eventual array failure. Cable 202 preferably has connectors on both ends. Transformer 703 provides the high voltage for the plasma array 100. Resistor 705 provides a high voltage monitor point for secondary voltage monitor 706. Secondary current monitor 704 connects to the cold side of the transformer secondary.

In a preferred embodiment, a variable voltage power source 506 is connected to the transformer primary center tap, and a pair of MOSFETs 708 provide balanced drive to the primary winding of transformer 703. Primary voltage and current amplitude and phase monitors 709 are used by controller 204 to provide the appropriate duty cycle and frequency for the transformer.

In an alternative embodiment, the transformer driver can be configured as an oscillator, so the transformer operates at the resonant frequency by default. In this case, a signal from the transformer driver is sent to the controller to synchronize the measurement of voltages and currents. This is can be used for accurate power measurement, for instance.

In another embodiment, the power supply 500 comprises a resonant transformer 201, with a half bridge driver on the transformer primary. See FIG. 17. The transformer primary bias is derived from a boost converter 212, which is connected to a power source. The power source can be internal to the power supply, such as a battery 208, or external to it such as a cell phone charger connected to mains power, or a vehicle power outlet. For precise power monitoring, the transformer secondary voltage is monitored through capacitors 205 and 206. The secondary current is monitored through sense resistor 207.

In one example, a typical large array (for example an array with closely spaced emitters in an area of about 2.5 inches by 6 inches) combined with a 4 foot length of RG-178 coaxial cable will have a typical capacitance of 720 pF. The step-up transformer 201 resonates with a capacitive load consisting of the coaxial cable 202 and the planar microplasma array 100. The main power source is a rechargeable lithium battery 208. This is charged through USB connector 223, which also is an external data interface to controller 204.

To allow the array power to be rapidly shut off in the case of over-current caused by array failure, the boost converter 212 switching element is driven by the controller 204. Capacitor 211 provides charge storage for high current pulses through the boost inductor 212. Switching element 213 may be driven through an amplifier to obtain additional drive current and/or voltage. The boosted flyback voltage is rectified by diode 214 and filtered by capacitor 215. Resistor 216 drops the voltage to a suitable range for the controller 204.

Inductor 217 is optional, but allows a higher duty cycle on the drive switching elements 218, reducing switching element loss while improving the spectral purity of the transformer output for EMC compatibility. The transformer primary voltage is sampled through resistor 219 to determine the transformer resonant frequency in auto-tuning mode.

Figure 19:
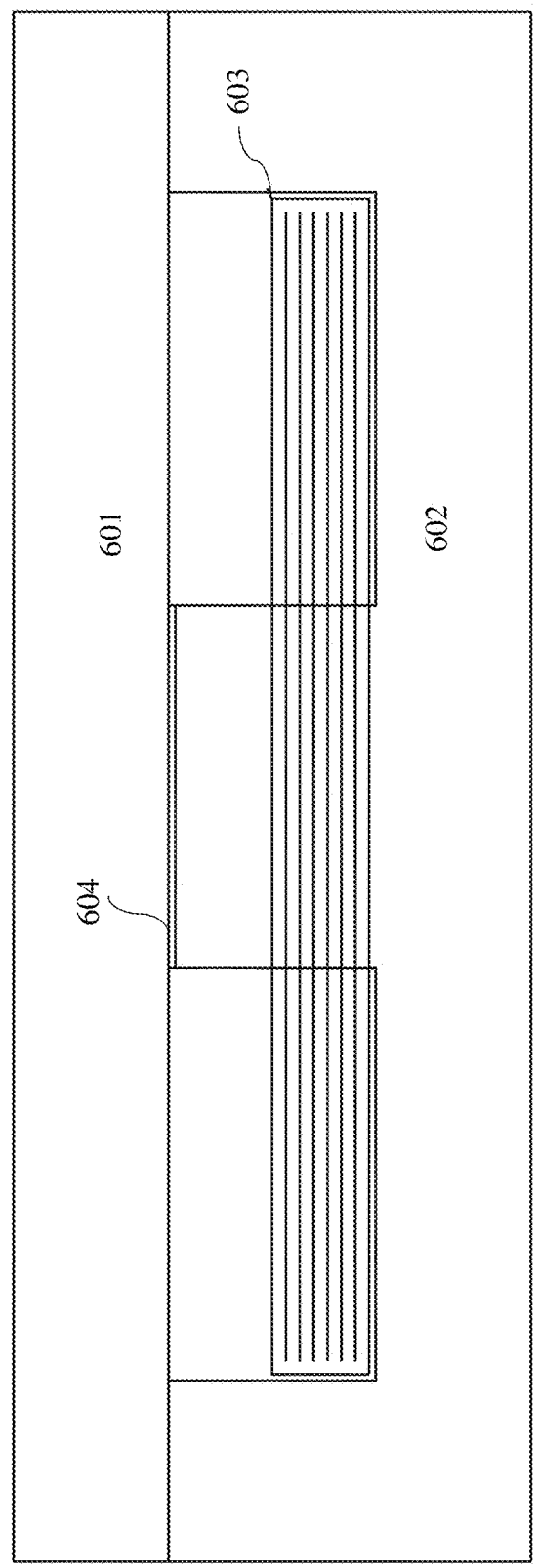
FIG. 19 is a cross-sectional view of a preferred embodiment of a planar transformer.

The preferred embodiment uses a planar transformer with "EI" type core. See FIG. 19. The "I" side 601 is placed at the top, away from the winding PCB 603. The "E" side 602 is placed at the bottom. This places the air gap 604, used to set the transformer inductance, to the top rather than the middle of the core. The magnetic flux concentrated around the air gap will increase AC loss, so the transformer windings, particularly the primary winding, are placed as far as possible from the air gap. A typical transformer design uses a planar ferrite core with a 12 layer FR-4 PCB. With a 135:1:1 turns ratio, a typical large array will operate at 50 kHz with an air gap $A_L$ value of 700 nH/$N^2$.

The preferred embodiment uses a controller, such as a microcontroller, FPGA or CPLD, to directly control the current switching on the transformer primary winding. This is typically between 50 kHz and 500 kHz, using a pair of N-channel MOSFETs. A buffer amplifier may be used to increase the gate drive voltage and/or current. The advantage of this arrangement is the ability of the controller to instantly stop switching in the event of an over-current condition caused by array failure.

The preferred embodiment is powered from lithium cells, with a supply voltage between 2.8 and 4.2V. See FIG. 17. The transformer primary center tap voltage is derived from a boost converter 212, with current being switched using a N-channel MOSFET. A buffer amplifier may be used to increase the gate drive voltage and/or current. In the preferred embodiment, the duty cycle of each transformer FET is 50%, operating in a balanced configuration. The boost converter 212 is operated at twice the frequency of the transformer drive, and is driven by the controller 204. Any ripple on the transformer center tap will be the same instantaneous value for either side being switched.

An alternate embodiment connects the transformer primary balanced driver in a cross connected feedback such that the driver automatically operates at the transformer resonant frequency. However, this requires additional electronic components to allow rapid shutdown, synchronization with the boost converter, and synchronization with the controller. In a typical embodiment, interrupt signals to the controller would be generated by both legs of the transformer primary.

In the preferred embodiment, the controller determines the transformer resonant frequency as follows. In this auto-tuning mode, the controller reduces the transformer drive duty cycle to a small value to protect the electronics. With a step-up transformer having a secondary winding with more turns than its primary winding, the output voltage is increased. For a given drive frequency, the controller measures the plasma drive voltage on the transformer secondary. If the voltage phase on the transformer primary leads the drive signal, the frequency is too high. The controller performs a frequency sweep to find the highest resonant peak. An alternate method is to compare the waveform on one leg of the transformer primary with the corresponding gate drive waveform, and adjust the drive frequency in a binary search to determine the frequency for switching at zero crossing. This will occur at the transformer resonant frequency.

Drive power into the array 100 is determined by measurements of voltage and current on the transformer secondary. The plasma initiation voltage is influenced by humidity and air pressure, so an accurate voltage measurement is desirable. In the preferred embodiment, transformer secondary current is sensed across a low value resistor.

Figure 21:
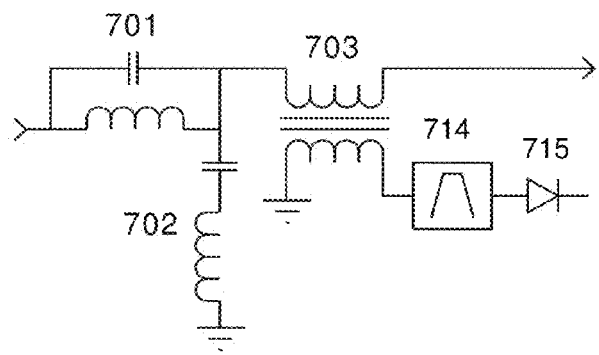
FIG. 21 is a schematic diagram of a circuit for reverse power detection.

An alternate method of measuring the plasma power in the array is to measure the reflected ("reverse") power at a high harmonic frequency. Since the plasma array has a high AC voltage across a relatively large capacitance, the amount of reactive power in the dielectric is very large compared to the amount of real power in the plasma. Therefore, measuring real power dissipation in the plasma is very difficult if measured at the fundamental drive frequency. Because the I/V curve of the plasma is nonlinear, while the capacitance of the array is relatively flat versus voltage, the measurement is much easier at a high harmonic of the drive frequency. A practical measurement frequency is 10.7 MHz because of the availability of inexpensive ceramic filters. This also reduces the size of components in the resonant circuits. Precise tuning is required, so the inductors preferably have non-magnetic cores for tighter tolerance. This simplifies the problem of isolating the large reactive component of the array load, and any power loss from dielectric heating in the array, from the effect of the plasma. A typical embodiment will use parallel resonant element tuned LC circuit 701 to block energy from the driver at 10.7 MHz. See FIG. 21.

Series resonant element tuned LC circuit 702 provides a low impedance current return at 10.7 MHz. Transformer 703 provides high voltage isolation and performs current to voltage conversion at 10.7 MHz. Filter 714 blocks harmonics from the driver that are not blocked by the resonant circuits. Detector 715 is preferably a logarithmic detector to allow measurement over a large power range. Because of the interwinding capacitance of the high voltage transformer which can pass harmonic energy at 10.7 MHz, a parallel tuned LC circuit 701 is used to block this. Series tuned LC circuit 702 provides a low impedance at 10.7 MHz, which allows current measurement through transformer 703. The capacitor in the series tuned LC circuit 702 will typically be rated at 1.5 kV. In a typical embodiment, transformer 703 is bifilar wound PTFE insulated wire around a ferrite bar. Since isolation of 1 kV AC is required, the windings are typically covered by insulating varnish to prevent air discharge between windings. Filter 714 is needed to remove harmonic energy that is not blocked by the tuned circuits. Detector 715 is typically a log detector. When a means of measuring the relative level of high harmonic reverse power at a high resolution is provided in the plasma driver, it can be used to set a constant plasma power level regardless of humidity or air pressure.

In a stand-alone driver, a housing 501 contains the power supply 500, a user interface 222, one or more inputs to the power supply, and one or more outputs to the array. See FIG. 16. Inputs include a USB port 223, an HMDI port, a headphone jack 224, a micro-USB jack, a lightening jack, and touch buttons or a touchscreen. Outputs to the array include a headphone jack 224, a micro-USB jack, a lightening jack, and multi-pin jacks. An audio transducer may be used to aid the visually impaired. In a wearable application, a vibrator may be added for discrete user feedback. In a battery-powered device, the housing also contains the battery, which may be either a primary or rechargeable battery. An embodiment connecting through USB may not need a battery, because the USB port may be used for input and battery charging.

The user interface will typically be a small LCD display 222. Bluetooth hardware can also be added for convenient connection to a smartphone. The controller 204 is connected to the user interface 222. In a preferred embodiment, a multicolor LED will indicate operating modes, including battery charging. While some embodiments of the driver use pre-programmed memory so that operating parameters that cannot be changed, other embodiments are programmable. The inputs can be used to program plasma operating parameters such as operating time and power level. The USB connection can also be used to set up additional features such as WiFi connection to a defined SSID and network password. However, a user's complete freedom to control the array 100 may not be the best solution for all embodiments.

In a preferred embodiment, the device is configured to emit plasma in a prescribed a treatment protocol provided by a physician, pharmacist, or clinician, much like a conventional prescription for medicines used with other drug delivery devices. The device may also retrieve patient information. The driver and array can be configured in a number of ways to do so. See FIG. 23A-D. In general, the prescriber connects a low-cost adapter board or dongle to a computing device. A software application running on the computing device performs authentication, loads recorded data, and programs the prescription. Data from treatments is recorded on the adapter board or dongle for upload to a computing device after the treatment. This data can be used post-treatment to determine efficacy and verify that the prescription was applied. For better control, and to promote a controlled business model, prescribers can be limited to downloading prescriptions from a central database rather than entering them directly.

In one embodiment a mobile computing device 610 is connected to an adapter board 225, which in turn is connected to a dongle 220 that is connected by cable 202 to the array. See FIG. 23A. Adapter board 225 functions as a physician's prescription book which contains authentication code registered per physician, clinician, pharmacist or pharmacy. Adapter board 225 is also a gatekeeper between encrypted protocols and user's privacy data being uploaded and downloaded from dongle 220. The adapter board 225 has an MCU onboard to interface between the dongle 220 and proprietary software applications installed on a mobile computing device or a desktop computer.

The dongle 220 includes settings for power, modulation details and time of a desired treatment. Thus the dongle 220 can be programmed with a treatment prescription for use with a driver. The dongle 220 may include an identification feature that is ensures that the driver is being used with the array of the appropriate size or shape for the desired treatment or patient. In a preferred embodiment the identification feature is a chip encoded with an embedded code that acts as an authentication handshake between the array 100 and the dongle 220 to make sure that only authorized arrays are used with a given power supply. In another embodiment the connector on the array has a physical shape mated to the connector on the power supply such that only devices with matching connectors operate to generate a plasma.

To ensure the array emits energy at the desired parameters, in a preferred embodiment the array will work only if its embedded identification code matches the dongle. For example, a programmed dongle 220 and its mated array may be given to a patient with the patient's prescription. The patient then attaches the dongle 220 to a power supply, whether it is a specialized device or a mobile computing device, and powers the plasma array to treat with plasma energy. Without the required code, the array will not be operational. Thus, the drivers can be sold with no prescription over the counter, much like fabric bandages such as BandAids®, and mated with a prescription dongle 220 and array when needed. Physicians and pharmacists may program the dongle 220 directly with customized protocols or they may program them with common protocols stored in a centralized prescription database. The dongle 220 can be programmed to record parameters of the treatment which may be evaluated post-treatment to verify that the prescription was applied and to judge its efficacy. See examples below.

In another embodiment, the mobile computing device 610 is connected to the adapter board 225, which in turn is connected to a cable 202 that is connected to the array. The function of the dongle, namely the prescription, is embedded on the array or in the cable. The integration of the dongle function onto the array 100 is referred to herein as a smart array 203. See FIG. 23B. Flash memory can be used to store the desired data on the array or in the cable. This may require a custom cable, but would allow a temperature sensor on the array as well. This may be important for some diabetic patients or others who have lost sensation and are insensitive to heat. Another alternate embodiment uses the memory of the mobile or desktop computing device.

In another embodiment, the driver 500 is connected to the dongle 220, which is connected by cable 202 to an array. See FIG. 23C. If using a smart array, the driver can be connected directly to it with a cable. See FIG. 23 D.

Figure 20:
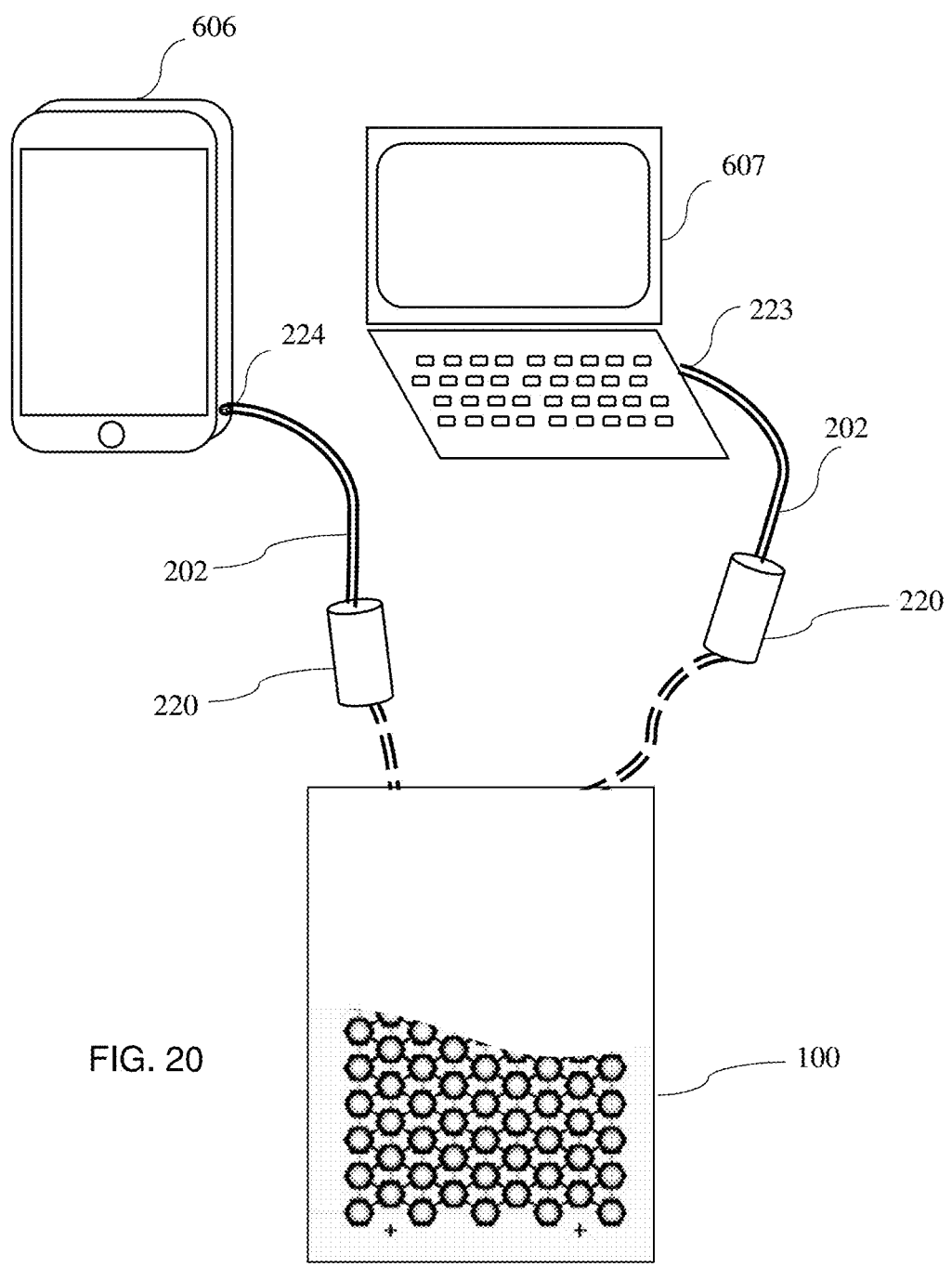
FIG. 20 is a front perspective view of an alternate power supply of the present invention connected to an array of plasma emitters, shown in a partial cut-away view.

Typically the mobile computing device is connected to the array 100 using its headphone jack 224 or USB port, but may be connected with a custom interface. Mobile computing devices include a smartphone 606, laptop computer 607, or tablet. On FIG. 20 the dashed line indicates that either the phone or laptop may be connected to the adapter board and the array. A desktop computer may also be used to powering and controlling the array. Mobile and desktop computing devices are programmable using onboard memory with a downloaded mobile application or installed program.

Plasma devices of the present invention can be used for treating many types of surfaces for purposes including cleaning, decontaminating, sterilization, and healing. For example:

Example 1: Decontamination of a Cell Phone

Individuals take cell phones where everywhere they go and are constantly using it after using the restroom, touching dirty door knobs, shaking others' hands, sharing the phone with others, and touching money. All these items are full of bacteria, which can spread to the individual's cell phone. Consequently, cell phones have up to 18 times more bacteria than a public restroom. In certain embodiments a non-thermal array 100 or smart array 203 can be placed around or incorporated into a cell phone. Once the non-thermal array 100 or smart array 203 is turned on the microorganisms on the phone will be inactivated, in effect sanitizing the cell phone from any infectious agents.

Example 2: Biological Warfare Decontamination Suit

In war biological weapons may be used against soldiers. In certain embodiments a biological warfare suit can be lined with non-thermal plasma arrays 100 or smart arrays 203. When a soldier has been contaminated with a biological weapon, the soldier can put on the non-thermal-plasma lined suit. Once the suit is on, the arrays 100 are turned on and the soldier can be decontaminated. The suit is reusable.

Example 3: Killing Fungus or Bacteria with a Non-Thermal Plasma Device

A voltage supplied to a plasma array can be modulated (pulsed or keyed on and off) at a rate of about 1 Hz to about 10 kHz. Specific modulation frequencies (the so-called Rife frequencies) have therapeutic effects in which a specific frequency is correlated to kill a specific microorganisms, including forms of bacteria, virus, fungus, mold, etc. The controller can use these frequencies to produce biological effects beyond those produced by reactive oxygen species and reactive nitrogen species. The resulting biological effects created by a non-thermal plasma array over a large surface area can eliminate microorganisms on any surface type.

Example 4: Method for Creating Ozone

Ozone is an unstable, but highly beneficial molecule, and is created by plasma. Plasma is a mixture of neutral and charged particles. When a voltage is applied to an array 100 of plasma emitters 107 that are in a gas containing oxygen, the plasma emitters generate a transfer of electrons that generates ozone. Ozone can be applied to a human body for therapeutic effects, to water for oxidizing pathogens and synthetics residues in the body, and to olive oil for ingesting which gives an individual a steady internal application of ozone. In addition, ozone can be used as an air disinfectant killing germs, infectious microorganisms, and neutralizing many biological problems like bacteria, viruses, mold and chemical outgassing.

Example 5: Cosmetic Treatments

Nitric oxide is a free-radical that has been shown to be beneficial in treating photodamaged facial skin by burning the old damaged skin cells so they can be sloughed off and replaced with new, healthy skin cells. An array of plasma emitters that are in a gas containing nitrogen are placed on the desired treatment area of the skin and the plasma emitters generate nitric oxide across the entire treatment area. In this was treatment using the present device is much faster than the conventional method of treating the area with plasma plume that is repeatedly passed, or scanned, across the treatment area.

Example 6—Treating *Pseudomonas aeruginosa*

In one example a power supply is used in conjunction with an array to treat a patient who has *Pseudomonas aeruginosa*, a multidrug-resistant pathogen, on her foot. A physician prescribes plasma treatment of 241 Hz for 10 minutes, twice a day for seven days. The pharmacist receives the prescription per treatment from physician, connects an adapter board 225 to a desktop computer, and programs the dongle 220 directly with an authentication code and instructions to operate the plasma-emitter array at 241 Hz for 10 minutes. The patient obtains the programmed dongle and mated array, or smart array 203, from the pharmacist, attaches it to a power supply such as a cell phone charger. The patient places the array on her foot where the infection is. The power supply confirms that it has been attached to an authorized array and initiates treatment. The patient leaves the array in place for the 10 minute treatment duration per the programmed protocol. When the 10 minutes has elapsed the patient removes the array from her foot. The patient repeats the treatment twice a day for six more days. The dongle and array, or smart array, can be returned to the pharmacist for uploading usage data of past treatments and reprogramed with new protocols for re-use.

Example 7—Treating *Candida albicans*

In another example a power supply is used in conjunction with an array to treat a patient who has *Candida albicans*, a fungal infection typically of the mouth or genitals. A physician prescribes plasma treatment of 482 Hz for 10 minutes, applied twice a day for seven days. The pharmacist receives the prescription, connects an adapter board 225 to a desktop computer, and programs the dongle 220 directly with an authentication code, and instructions to operate the plasma-emitter array at 482 Hz for 10 minutes. The patient obtains the programmed dongle, cable and attached plasma array from the pharmacist, and attaches it to a driver. The driver is portable and chargeable using an USB wall charger. The driver confirms that it has been attached to an authorized array and initiates treatment. The patient leaves the array in place for the 10 minute treatment duration. When the 10 minutes has elapsed the patient removes the array from her mouth. The patient repeats the treatment once a day for six more days. The dongle and array, or smart array, can be returned to the pharmacist for uploading usage data of past treatments and reprogramed with new protocols for re-use.

Example 8—Treating *Trichophyton rubrum*

In another example a power supply is used in conjunction with an array to treat a patient who has *Trichophyton rubrum*, a fungus that is the most common cause of athlete's foot, fungal infection of toenails, jock itch, and ringworm. The treatment is 775 Hz for 10 minutes, for three treatments per day, until the symptoms go away. The patient purchases over-the-counter a power supply, dongle and arrays that are customized to provide a limited number of treatments. For example, for toenail fungus, the patient purchases a device that can provide up to twenty 10 minute treatments of plasma at 775 Hz. The patient applies the plasma array to his infected toenail for 10 minutes each day until the symptoms go away.

Example 8—Treating *Trichophyton metagrophyte*

In another example a plugged cable is used in conjunction with an array to treat *Trichophyton metagrophyte*, another cause of various human skin infections and also of a skin infection in mice. A dongle is programmed using a desktop computer connected to an adapter board that has access to the internet. An authorized user downloads a protocol from a treatment database to the dongle then causes the power supply to provide plasma treatments at a given time, frequency, and duration such as 775 Hz for up to 10 minutes per treatment, three times per day for 4 weeks. The dongle and array, or smart array, can be returned to the pharmacist for uploading usage data of past treatments and reprogramed with new protocols for re-use.

While there has been illustrated and described what is at present considered to be the preferred embodiments of the present invention, it will be understood by those skilled in the art that various changes and modifications may be made and equivalents may be substituted for elements thereof without departing from the true scope of the invention. The embodiments of the invention described herein are not intended to be exhaustive or to limit the invention to precise forms disclosed. Rather, the embodiments selected for description have been chosen to enable one skilled in the art to practice the invention. Therefore, it is intended that this invention not be limited to the particular embodiments disclosed, but that the invention includes all embodiments falling within the scope of the appended claims.

We claim:

1. A device for controlling an array of non-thermal plasma emitters, the array having a capacitance, the device comprising:
    a power supply connectable to the array with a cable having a capacitance, wherein the sum of the capacitance of the array and the capacitance of the cable is a combined capacitance;
    the power supply operates at the resonant frequency of the combined capacitance; and
    an identification feature that permits the device to operate only authorized arrays.

2. The device of claim 1 wherein the power supply comprises:
    a. a controller;
    b. a step-up transformer; and
    c. a balanced driver.

3. The device of claim 1 further comprising memory for storing one or more parameters for operation of the array.

4. The device according to claim 1 wherein the power supply further comprises a battery.

5. The device according to claim 1 wherein power supply further comprises a power source, and the power source and controller are in a mobile computing device.

6. The device of claim 1 wherein the array comprises a flexible substrate.

7. A device for controlling an array of non-thermal plasma emitters, the array having a capacitance, the device comprising:
   a. a power supply comprising:
   b. a controller;
   c. a step-up transformer having a primary winding and a secondary winding;
   d. a balanced driver; and
   e. a cable connecting the power supply to the array, the cable having a capacitance;
   wherein the controller measures the voltage on the primary winding and compares it to the voltage on the secondary winding to determine a resonant frequency of the device.

8. The device of claim 7 wherein the resonant frequency is sum of the capacitance of the array and the capacitance of the cable.

9. The device of claim 7 further comprising memory for storing one or more parameters for operation of the array.

10. A device for controlling an array of non-thermal plasma emitters, the array having a capacitance, the device comprising:
    a. a mobile computing device connectable to the array using a cable having a capacitance;
    b. a controller and a power source in the mobile computing device; and
    c. an identification feature that permits the mobile computing device to operate only authorized arrays.

11. The device of claim 10 wherein the sum of the capacitance of the array and the capacitance of the cable is a combined capacitance and the power source operates at the resonant frequency of the combined capacitance.

12. The device of claim 10 further comprising memory for storing one or more parameters for operation of the array.

13. The device of claim 12 wherein the memory is in the mobile computing device and is programmable.

14. The device of claim 10 wherein the identification feature is embedded in a dongle disposed on the cable.

15. A device for controlling an array of non-thermal plasma emitters, the array having a capacitance, the device comprising:
    a. a housing comprising:
       i. user interface;
       ii. one or more inputs;
       iii. one or more outputs;
       iv. a power supply, wherein the power supply comprises:
           a. a controller,
           b. a step-up transformer having a primary winding and a secondary winding, and
           c. a balanced driver;
       v. memory for storing one or more parameters for operation of the array; and
    b. a cable connecting the housing at an output to the array, the cable having a capacitance;
    wherein the sum of the capacitance of the array and the capacitance of the cable is a combined capacitance; and
    wherein the power supply operates at a resonant frequency of the combined capacitance.

16. The device of claim 15 further comprising an identification feature that permits the power supply to operate only authorized arrays.

17. The device of claim 15 wherein the controller measures the voltage on the primary winding and compares it to the voltage on the secondary winding to determine the resonant frequency.

18. The device of claim 15 wherein the memory is programmable via an input.

* * * * *